(12) United States Patent
Collu et al.

(10) Patent No.: US 12,410,383 B2
(45) Date of Patent: Sep. 9, 2025

(54) PROCESS OF MAKING A TREATMENT COMPOSITION THAT INCLUDES A PLANT ROSIN MATERIAL AND RELATED PREMIX COMPOSITIONS

(71) Applicant: The Procter & Gamble Company, Cincinnati, OH (US)

(72) Inventors: Mattia Collu, Saint-Gilles (BE); Cédric Marc Tahon, Oost-Vlaanderen (BE); Johan Smets, Lubbeek (BE); Jef Annie Alfons Maes, Sint-Niklaas (BE); Ilse Maria Cyrilla D'Haeseleer, Dendermonde (BE); Katrien Maria Nuyts, Brussels (BE); Abel Jerez Gomez, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 719 days.

(21) Appl. No.: 17/549,919

(22) Filed: Dec. 14, 2021

(65) Prior Publication Data

US 2022/0186148 A1    Jun. 16, 2022

Related U.S. Application Data

(60) Provisional application No. 63/125,987, filed on Dec. 16, 2020.

(51) Int. Cl.
| | | |
|---|---|---|
| *C11D 1/00* | (2006.01) | |
| *C11D 3/00* | (2006.01) | |
| *C11D 3/38* | (2006.01) | |
| *C11D 3/382* | (2006.01) | |
| *C11D 3/50* | (2006.01) | |
| *C11D 11/00* | (2006.01) | |

(52) U.S. Cl.
CPC ............ *C11D 3/382* (2013.01); *C11D 3/0015* (2013.01); *C11D 3/50* (2013.01)

(58) Field of Classification Search
CPC ........... C11D 1/00; C11D 3/0015; C11D 3/38; C11D 3/382; C11D 3/50; C11D 3/505; C11D 11/00; C11D 11/0064
See application file for complete search history.

(56) References Cited

U.S. PATENT DOCUMENTS

| | | |
|---|---|---|
| 2,571,689 A | 10/1951 | Maria et al. |
| 2,776,276 A | 1/1957 | Glasebrook et al. |
| | (Continued) | |

FOREIGN PATENT DOCUMENTS

| | | |
|---|---|---|
| EP | 0138597 A2 | 4/1985 |
| EP | 1038910 A1 | 9/2000 |
| | (Continued) | |

OTHER PUBLICATIONS

All Office Actions; U.S. Appl. No. 17/549,922, filed Dec. 14, 2021.
(Continued)

*Primary Examiner* — Brian P Mruk
(74) *Attorney, Agent, or Firm* — Carolyn S. Powell

(57) ABSTRACT

Processes of making treatment compositions that include plant rosin materials and one or more benefit agents, such as perfume raw materials. Related premix compositions. Treatment compositions made from such processes and premixes.

19 Claims, 7 Drawing Sheets

(56) References Cited

U.S. PATENT DOCUMENTS

| | | | |
|---|---|---|---|
| 3,950,510 A | 4/1976 | Adams | |
| 5,362,715 A | 11/1994 | Cohen | |
| 5,478,567 A | 12/1995 | Nakagawa et al. | |
| 6,869,923 B1 | 3/2005 | Cunningham | |
| 7,438,897 B2 | 10/2008 | Gupta | |
| 7,795,476 B2 * | 9/2010 | Corzani | C08L 71/02 568/617 |
| 8,802,729 B2 | 8/2014 | Fenyvesi et al. | |
| 9,186,642 B2 | 11/2015 | Dihora | |
| 10,582,705 B2 | 3/2020 | Conover | |
| 2002/0018760 A1 | 2/2002 | Vatter et al. | |
| 2004/0121926 A1 | 6/2004 | Waits et al. | |
| 2006/0020057 A1 | 1/2006 | Maas et al. | |
| 2006/0154850 A1 * | 7/2006 | Quellet | C11D 3/502 512/2 |
| 2007/0129476 A1 | 6/2007 | Macbeath et al. | |
| 2010/0089420 A1 | 4/2010 | Greenberg | |
| 2013/0125297 A1 | 5/2013 | Pagani | |
| 2019/0153354 A1 | 5/2019 | Lankin et al. | |
| 2019/0373883 A1 | 12/2019 | Conover | |

FOREIGN PATENT DOCUMENTS

| | | | | |
|---|---|---|---|---|
| EP | 2746379 | * | 6/2014 | C11D 11/0094 |
| EP | 2746379 A1 | * | 6/2014 | C11D 11/0094 |
| GB | 1340043 A | | 12/1973 | |
| GB | 1349741 A | | 4/1974 | |
| GB | 1419116 A | | 12/1975 | |
| GB | 1515299 A | | 6/1978 | |
| IT | 202000004684 A1 | | 9/2021 | |
| JP | 2001262199 A | | 9/2001 | |
| WO | 2011030158 A2 | | 3/2011 | |
| WO | 2019051165 A1 | | 3/2019 | |
| WO | 2020058373 A1 | | 3/2020 | |
| WO | 2020234263 A1 | | 11/2020 | |

OTHER PUBLICATIONS

All Office Actions; U.S. Appl. No. 17/549,916, filed Dec. 14, 2021.
All Office Actions; U.S. Appl. No. 17/549,923, filed Dec. 14, 2021.
Glycerol ester of wood rosin INV, XP55811290 Retrieved from the Internet URL:https://en.wikipedia.org/wiki/Glycerol ester of wood rosin, dated Mar. 4, 2021, p. 2.
Database GNPD Mintel,"Moist Diane Extra Moist & Shine Hair Mask has been relaunched", http:llwww.gnpd.comT, dated Jan. 29, 2020 pp. 3.
Eastman rosin products, "Natural resins for adhesion, wetting, viscocity control", pp. 08.
Mahmoud Abdul-Raheim,"BAOJ Chemistry Rosin Chemistry, Derivatives, and Applications a review", vol. 4, dated 2018, p. 2 of 16.
Polymer Properties Database, "Rosin Esters and Polymers", https://polymerdatabase.com/polymer classes/Rosin.html, dated 2015, pp. 03.
Satish Kumar Gupta,"Rosin: a naturally derived excipient in drug delivery systems, Department of Pharmaceutical Technology", dated 2013, pp. 05.
Unpublished U.S. Appl. No. 17/549,916, filed Dec. 14, 2021, to first inventor Mattia Collu et al.
Unpublished U.S. Appl. No. 17/549,922, filed Dec. 14, 2021, to first inventor Mattia Collu et al.
Unpublished U.S. Appl. No. 17/549,923, filed Dec. 14, 2021, to first inventor Mattia Collu et al.
PCT Search Report and Written Opinion for PCT/US2021/072889 dated Apr. 26, 2022, 13 pages.
Bambang Wiyono et al. "Chemical Compositions of Pine Resin, Rosin and Turpentine Oil from West Java", Journal of Forestry Research, vol. 3, No. 1, dated Mar. 1, 2016; pp. 7-17.
Database GNPD Mintel; "Foundation EX SPF 50+ PA++++", http://www.gnpd.com, dated May 2020; 5 Pages.
Database GNPD Mintel; "Hair Color Treatment", http://www.gnpd.com; dated Nov. 17, 2016; 4 Pages.
Database GNPD Mintel; "Light Luminous Hydrating Lipstik" http;//www.gnpd.com; dated Jul. 1, 2020; 4 Pages.
Database GNPD Mintel; "Moisturizing Lip Balm", http;//www.gnpd.com, dated Nov. 10, 2020 , 3 Pages.
Database GNPD Mintel; "Shaving Oil", http://www.gnpd.com, dated May 2, 2018 , 5 Pages.

* cited by examiner

PROCESS OF MAKING A TREATMENT COMPOSITION THAT INCLUDES A PLANT ROSIN MATERIAL AND RELATED PREMIX COMPOSITIONS

This application claims benefit of Provisional Ser. No. 63/125,987, filed on Dec. 16, 2020.

FIELD OF THE INVENTION

The present disclosure relates to processes of making treatment compositions that include plant rosin materials and one or more benefit agents, such as perfume. The present disclosure also relates to related premix compositions, as well as treatment compositions made from such processes and premixes.

BACKGROUND OF THE INVENTION

Manufacturers of treatment compositions, such as liquid fabric softeners, often use additives to increase the performance profile of certain benefit agents. For example, deposition aids may be used to increase the deposition, and subsequent performance, of benefit agents, such as perfume.

When selecting additives that promote such benefits, manufacturers and consumers may prefer naturally derived materials for environmental reasons.

Furthermore, manufacturers seek not only effective ingredients but also effective processes for incorporating those ingredients into final product compositions. Preferred processing steps increase the efficacy of the ingredients without requiring an increase of ingredients or complexity.

There is a need for processes and/or intermediates that relate to naturally derived ingredients, resulting in improved treatment compositions.

SUMMARY OF THE INVENTION

The present disclosure relates to processes of making a treatment composition, where the process includes the steps of: providing a base composition, where the base composition includes an adjunct material; and adding a plant rosin material and one or more benefit agents to the base composition, where the plant rosin material is added with or after the one or more benefit agents.

The present disclosure also relates to treatment compositions made from such processes.

The present disclosure also relates to premix compositions, which may be useful in the processes of the present disclosure, may include: from about 5% to about 95% of a plant rosin material, and from about 5% to about 95% of one or more benefit agents, preferably where the one or more benefit agents comprises fragrance material, where the plant rosin material and the one or more benefit agents are present in total in the premix composition at a level of from about 30% to about 100%, preferably from about 50% to about 100%, more preferably from about 75% to about 100%, by weight of the premix composition.

BRIEF DESCRIPTION OF THE DRAWINGS

The figures herein are illustrative in nature and are not intended to be limiting.

DETAILED DESCRIPTION OF THE INVENTION

Figure 1:
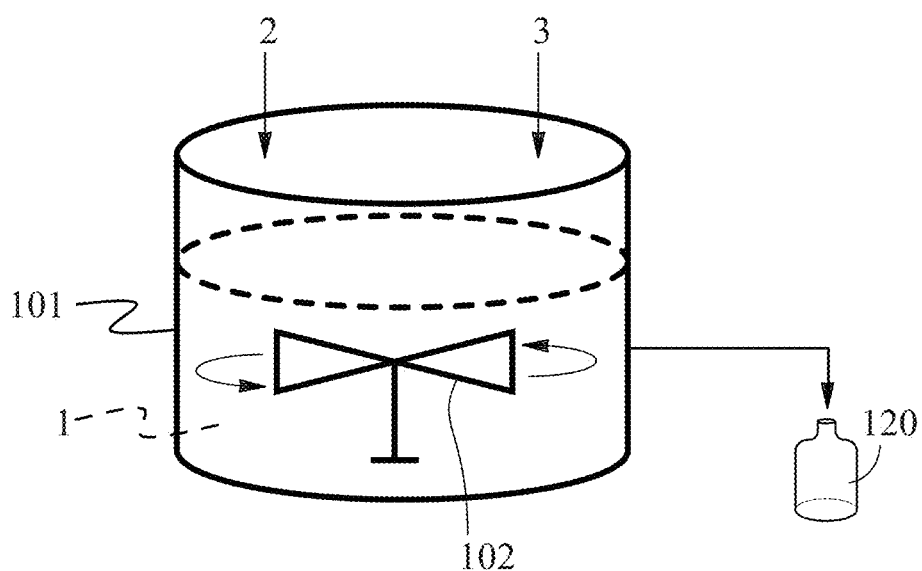
FIG. 1 shows a schematic drawing of a batch process according to the present disclosure.

The present disclosure relates to processes of making treatment compositions, as well as related premix compositions. The treatment compositions described herein comprise a plant rosin material and one or more benefit agents. The processes of the present disclosure describe preferred orders in which the components are combined. For example, the plant rosin material may be added with or after the one or more benefit agents to a base composition, preferably as a premix composition.

Without wishing to be bound by theory, it is believed that the preferred order of addition allows the benefit agent, such as perfume, to facilitate incorporation of the plant rosin material into the base composition. For example, it is believed that the perfume may enable the formation of self-assembled capsules in the finished product, leading to improved phase stability. Surprisingly, it has also been found that particular orders of addition can lead to improved performance of the resulting treatment composition.

The processes, components, and compositions of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein "consumer product," means baby care, beauty care, fabric & home care, family care, feminine care, and/or health care products or devices intended to be used or consumed in the form in which it is sold, and not intended for subsequent commercial manufacture or modification. Such products include but are not limited to diapers, bibs, wipes; products for and/or methods relating to treating human hair, including bleaching, coloring, dyeing, conditioning, shampooing, styling; deodorants and antiperspirants; personal cleansing; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; adult incontinence products; products and/or methods relating to oral care including toothpastes, tooth gels, tooth rinses, denture adhesives, tooth whitening; over-the-counter health care including cough and cold remedies; pest control products; and water purification.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Process of Making a Treatment Composition

The present disclosure relates to processes of making a treatment composition. As described in more detail below, the process may comprise the steps of providing a base composition that includes an adjunct material, and adding a plant rosin material and one or more benefit agents to the base composition. The plant rosin material may be added with or after the one or more benefit agents. The plant rosin material and the one or more benefit agents may be added as a single input stream, for example as a premix composition.

In the process of the present disclosure, the plant rosin material and the one or more benefit agents may be combined, separately or together as a premix, with the base composition via any suitable process, such as via a batch process, a continuous-loop addition process, or an in-line addition process, preferably an in-line addition process.

The process may comprise a batch process. FIG. 1 shows a schematic drawing of a batch process 100. A container 101 holds a base composition 1. To the container, a benefit agent 2, such as perfume, is added, as is a plant rosin material 3. The plant rosin material 3 is added with or after the benefit agent 2. The plant rosin material 3 may be added substantially concurrently with the benefit agent, for example as separate inputs, or preferably as a premix composition that includes the plant rosin material 3 and the benefit agent 2. The resulting mixture may be mixed via dynamic mixing, such as with a rotating impeller 102, and may be subsequently provided to a bottle 120, for example one that is suitable for sale to a consumer.

The process may preferably comprise an in-line addition process. In-line addition processes may be preferred to batch processes. In addition to known advantages such as being able to add differentiating ingredients (e.g., dyes) late in the manufacturing process to form different products, the lack of an air-liquid interface in an in-line addition process may result in less creaming and/or flocculation of the plant rosin material.

Figure 2:
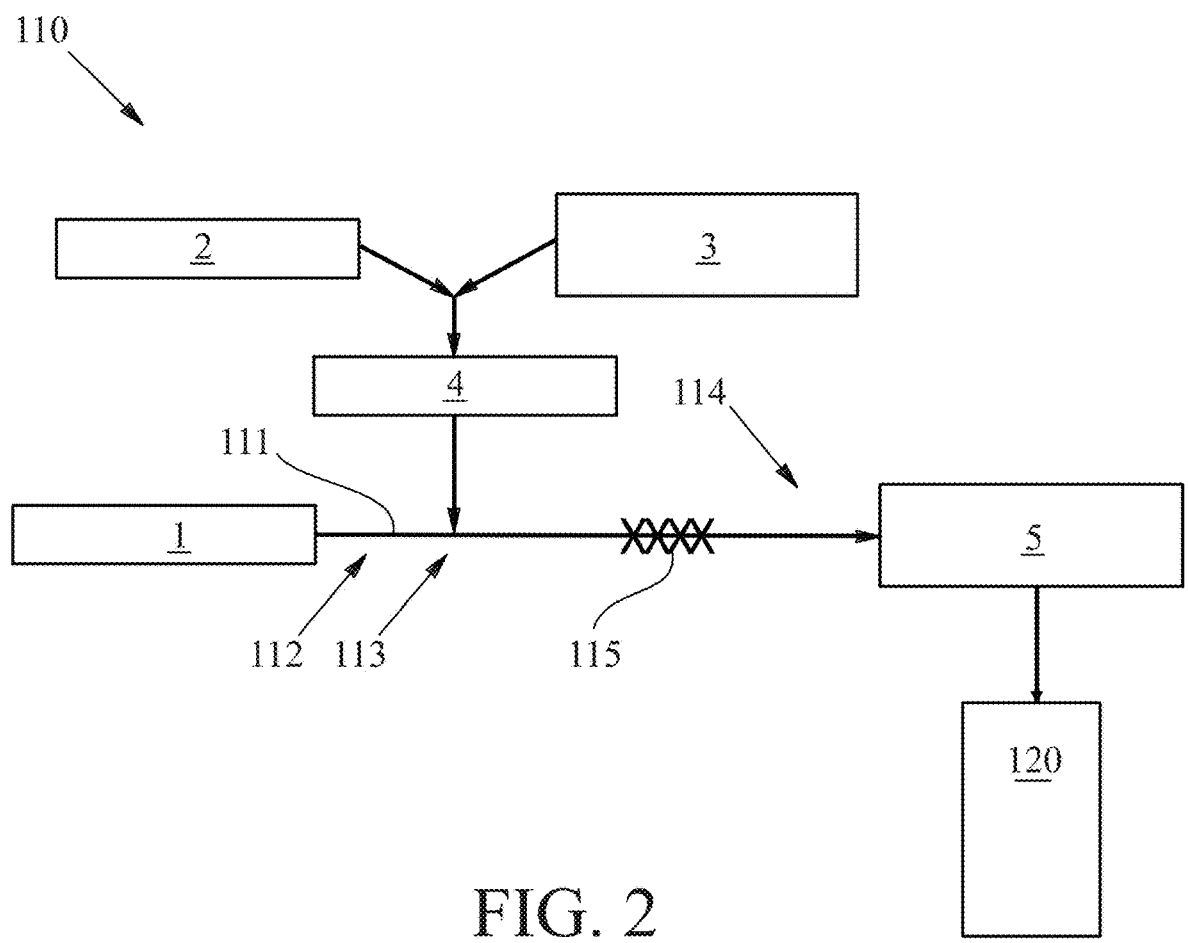
FIG. 2 shows a schematic drawing of an in-line addition process where the one or more benefit agents and the plant rosin material are added concurrently as a premix composition.

FIG. 2 shows a schematic drawing of an in-line addition process 110 where the one or more benefit agents 2 and the plant rosin material 3 are added concurrently as a premix composition 4. A base composition 1 is flowed from an upstream region 112 through a pipe 111. A premix composition 4 combined with the base composition 2 at a confluence region 113 that is downstream from the upstream region 112. The premix composition 4 comprises the one or more benefit agents 2 and the plant rosin material 3. The premix composition 4 may be pre-made and stored prior to its use in the in-line addition process, e.g., prior to addition to the pipe 111. Alternatively, the premix composition 4 may be made in an in-line process, where the plant rosin material 3 and the one or more benefit agent 2 are combined to form the premix composition 4 substantially immediately prior to combining the premix composition 4 with the base composition 1.

After the premix composition 4 has been combined with the base composition 1, the resulting mixture may be mixed, for example by passing it through a rotator-stator mixer 115. The resulting treatment composition 5 may be collected at a downstream region 114, for example in a bottle 120 suitable for sales to consumers.

Figure 3:
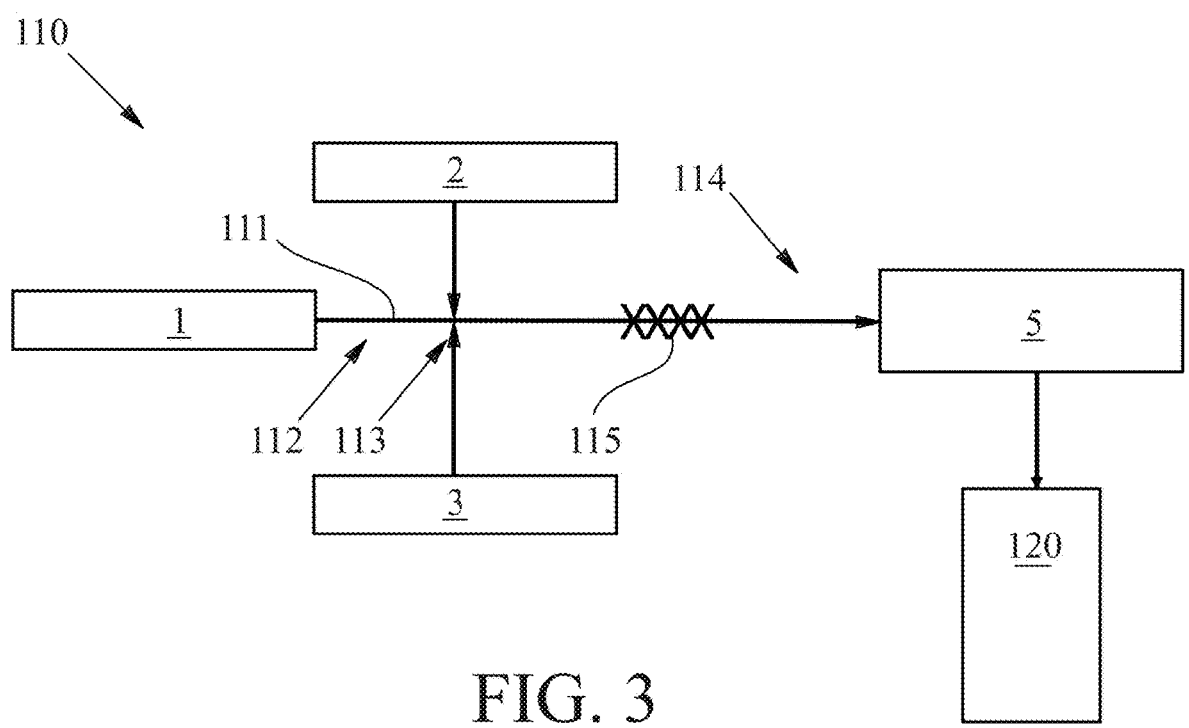
FIG. 3 shows a schematic drawing of an in-line addition process where the one or more benefit agents and the plant rosin material are added concurrently as separate inputs.

FIG. 3 shows a schematic drawing of an in-line addition process 110 where the one or more benefit agents 2 and the plant rosin material 3 are added concurrently as separate inputs. A base composition 1 is flowed from an upstream region 112 through a pipe 111. The one or more benefit agents 2 and the plant rosin material 3 may be combined with the base composition 1 at substantially the same time at a confluence region 113 that is downstream from the upstream region 112. The resulting mixture may be mixed, for example by passing through a rotator-stator mixer 115. The resulting treatment composition 5 may be collected at a downstream region 114, for example in a bottle 120 suitable for sales to consumers.

Figure 4:
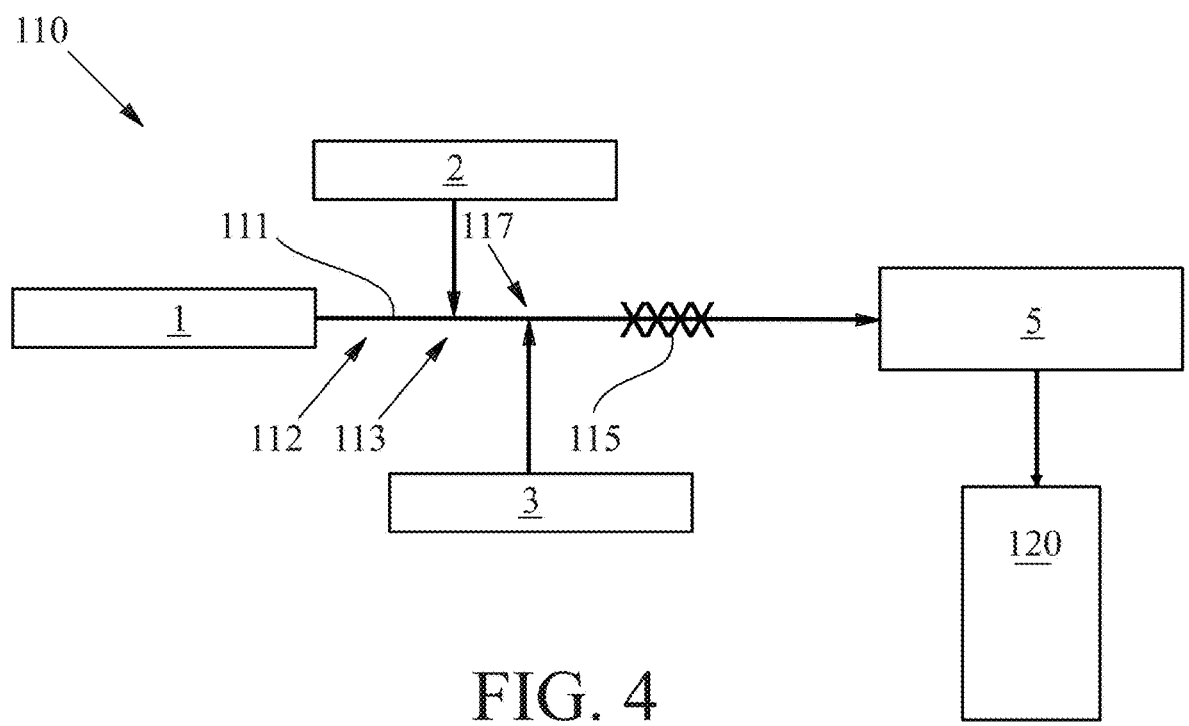
FIG. 4 shows a schematic drawing of an in-line addition process where the plant rosin material is added as a separate input after the one or more benefit agents have been added.

FIG. 4 shows a schematic drawing of an in-line addition process 110 where the plant rosin material 3 is added as a separate input after the one or more benefit agents 2 have been added. A base composition 2 is flowed from an upstream region 112 through a pipe 111. The one or more benefit agents 2 is combined with the base composition 1 prior to the plant rosin material 3 being combined with the base composition 1. Put another way, the plant rosin material 3 is added to the base composition 1 after the one or more benefit agents 2 have been added. The one or more benefit agents 2 are added to the base composition 1 at a location, for example at a first confluence region 116, that is relatively upstream from the location, for example a second confluence region 117, at which the plant rosin material 3 is added. The mixture may be mixed, for example by passing through a rotator-stator mixer 115. The resulting treatment composition 5 may be collected, for example in a bottle 120 suitable for sales to consumers.

Figure 5:
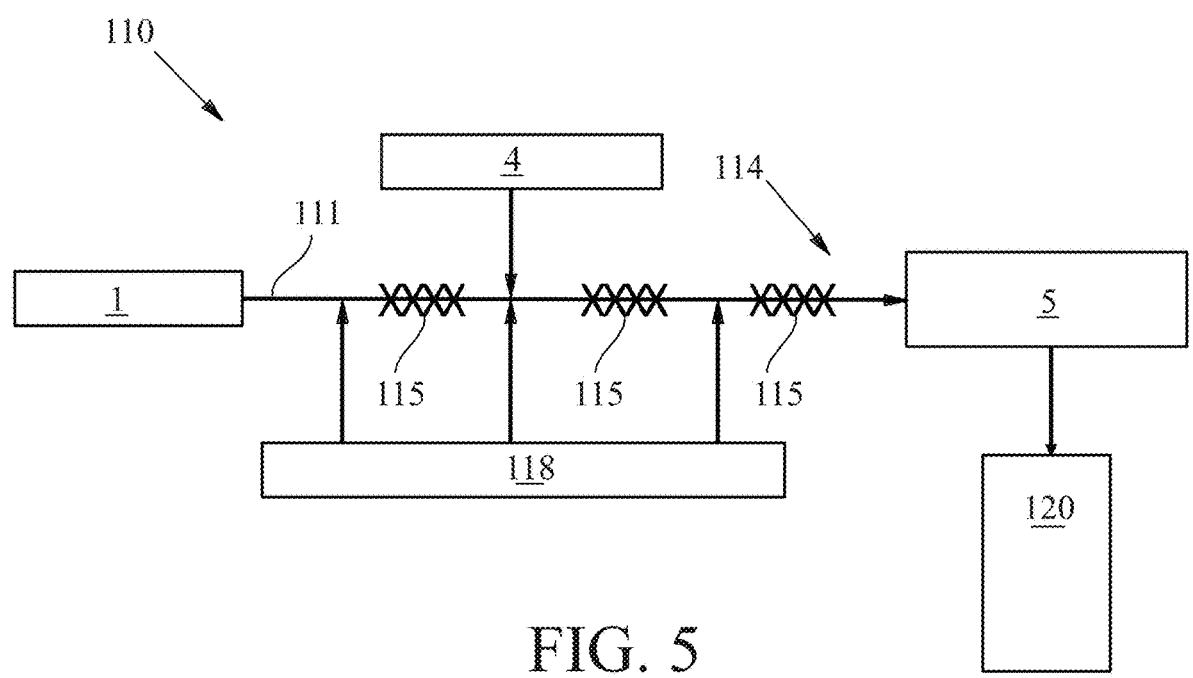
FIG. 5 shows a schematic drawing of an in-line addition process where adjunct ingredients may optionally be added at various points.

FIG. 5 shows a schematic drawing of an in-line addition process 110 where adjunct ingredients may optionally be added before and/or with and/or after the premix 4 (or alternatively, the one or more benefit agents 2 and the plant rosin material 3, added separately) is combined with the base composition 1. Mixing devices, such as rotator-stator mixers 115, may be used to mix the mixtures and ultimately form the treatment composition 5. The resulting treatment composition 5 may be collected, for example in a bottle 120 suitable for sales to consumers.

In an in-line addition process, any suitable dynamic mixer or static mixer may be used. Preferably, a dynamic mixer, more preferably a rotator-stator mixer, is used, as exemplified above, such as a Y-TRON Z™ homogenizer, available from YTRON Process Technology. Such mixers may be desired in order to better control the mixing energy, tangential velocity, and/or resulting particle size. In view of the high viscosities that may be associated with plant rosin materials, it is believed that rotator-stator mixers will be more convenient to use compared to static mixers.

As materials are added to the base composition, the mixture may be mixed with a mixer, preferably a rotator-stator mixer, having a tangential velocity of from about 7 m/s to about 19 m/s, preferably from about 12 m/s to about 16 m/s, more preferably about 14 m/s. Without wishing to be bound by theory, it is believed that selection of the correct tangential velocity can lead to desirable particle sizes formed from the plant rosin material and the benefit agent. Tangential velocities that are too low or too high may lead to particles that are too large or too small, respectively, leading to suboptimal performance of the treatment composition.

The process may further comprise a heating step. For example, the process may comprise the step of heating the plant rosin material above ambient temperature. The step of heating the plant rosin material above ambient temperature may occur prior to combining the plant rosin material with the one or more benefit agents, with the base composition, or both. The step may comprise heating the plant rosin material at least to the softening point of the plant rosin material. The step may comprise heating the plant rosin material to at least about 10° C., or at least about 20° C., or at least about 30° C., above the ambient temperature. The step may comprise heating the plant rosin material to above ambient temperature and between 1° C. and 30° C. below the softening point of the plant rosin material. The plant rosin material may be at a temperature above ambient temperature, preferably at a temperature equal to or greater than the softening point of the plant rosin material, when combined with the one or more benefit agents, the base combination, or both. It is believed that when the plant rosin material is heated to a certain degree, it become relatively easier to incorporate into the base composition or the premix composition. On the other hand, heating the plant rosin material may affect the stability of the one or more benefit agent, the base composition, and/or the treatment composition; for example, if the one or more benefit agent is relatively volatile (such as a perfume) or sensitive to heat (such as an enzyme), an elevated temperature may cause some of the benefit agent to be lost or degraded. To facilitate processing, it may be preferred to heat the plant resin material when the amount of plant rosin material and the benefit agent are present at weight ratios greater than 40:60, preferably greater than 50:50.

The plant rosin material and the benefit agent may be combined at ambient temperatures, for example from about 18° C. to about 25° C., or from about 18° C. to about 22° C. Combining the materials at ambient temperature may be particularly effective and preferred when there is more benefit agent than resin material. For example, the plant rosin material and the benefit agent may preferably be combined at ambient temperature when the weight ratio of plant rosin material to benefit agent (preferably perfume raw materials) is less than 50:50, preferably less than 40:60, more preferably less than 30:70, more preferably less than 20:80, or even less than 10:90.

To facilitate incorporation of the plant rosin material into the premix composition and/or the base composition, the plant rosin material be in particulate form. For example, the plant rosin material may be provided as a powder, for example, where the particles are characterized by an average diameter of less than 5 mm, or less than 3 mm, or less than 2 mm, or less than 1 mm, or from about 10 μm to about 500 μm. The process may comprise the step of grinding the plant rosin material into smaller particle sizes by any suitable method, preferably into particles having an average diameter of less than 5 mm, or less than 3 mm, or less than 2 mm, or less than 1 mm, or from about 10 μm to about 500 um. Plant rosin material having a relatively small particle size may more easily be incorporated into a premix or base composition without undue heating; this is of a particular benefit when combining with materials that are sensitive to heat (e.g., perfumes or enzymes).

The compositions and components of the processes are described in more detail below.

Base Composition

The processes of the present disclosure may comprise the step of providing a base composition. The base composition may comprise an adjunct ingredient. The one or more benefit agents and the plant rosin material are combined with, typically added to, the base composition.

The base composition may be in any suitable form. The base composition may be in the form of a liquid. When the base composition is a liquid, the one or more benefit agents and the plant rosin material may conveniently be mixed, for example, via a batch or in-line addition process.

The base composition may comprise water. The base composition may comprise at least 8% water, preferably at least 25% water, more preferably at least 50% water, more preferably at least 60% water, more preferably at least 70% water, more preferably at least 75% water, more preferably at least 80% water, more preferably at least 90% water, by weight of the base composition.

The base composition may be in the form of a solid. The one or more benefit agents and the plant rosin material may be added in any suitable manner, for example by spraying or an agglomeration process.

The base composition may comprise an adjunct ingredient. The adjunct ingredient may be present in the base composition when the base composition is provided. Additionally or alternatively, adjunct ingredients may optionally be added at any suitable point of the process, including before, during, or after the one or more benefit agents and the plant rosin material are added to the base composition. As discussed in more detail above, FIG. 5 shows a schematic drawing of an in-line addition process where adjunct ingredients may be added at one or more points of the process.

The adjunct ingredient(s) may be suitable for delivering a treatment benefit to a target surface, such as a fabric or other textile. Adjuncts ingredients, as used herein, may also include agents that facilitate chemical or physical stability in the treatment compositions, such as buffers, structurants/thickeners, and/or carriers.

The adjunct ingredient(s) may be present in the composition at levels suitable for the intended use of the composition. Typical usage levels range from as low as 0.001% by weight of composition for adjuncts such as optical brighteners to 50% by weight of composition for builders.

The adjunct ingredient may include an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, conditioning actives (such as fabric softening agents), carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof. The compositions of the present disclosure may include, among other things, an amine, a surfactant system, a conditioning agent, a water-binding agent, a sulfite, a structurant, organic solvent, free perfume, a perfume delivery system, or mixtures thereof. Several of these adjuncts are described in more detail below.

The adjunct ingredient may comprise a surfactant system, conditioning actives, or combinations thereof. Preferably, the surfactant system comprises anionic surfactant, nonionic surfactant, cationic surfactant, and/or zwitterionic surfactant. Preferably, the conditioning actives comprise a quaternary ammonium compound, silicone compounds, or both.

Compositions according to the present disclosure may include a surfactant system. The surfactant system may consist of one type of surfactant. The surfactant system may include more than one surfactant.

The compositions of the present disclosure may include from about 20% to about 75%, or from about 25% to about 70%, or from about 30% to about 50%, by weight of the composition, of a surfactant system. Compositions of the present disclosure may include less than 20%, or less than 10%, or less than 5%, or less than 3%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES) including sodium laureth sulfate (SLES), alkyl sulfates (AS) including sodium lauryl sulfate (SLS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine). In certain treatment compositions, for example, those that include a cationic material such as a fabric conditioning agent, it may be desirable to limit the amount of anionic surfactant present; for example, the treatment composition may comprise less than 5%, or less than 3%, or less than 1%, or less than 0.1%, or even 0%, by weight of the treatment composition, of anionic surfactant.

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

The compositions of the present disclosure may include a conditioning active. Compositions that contain conditioning actives may provide softness, anti-wrinkle, anti-static, conditioning, anti-stretch, color, and/or appearance benefits. Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof. Preferably, the treatment composition comprises a conditioning active that comprises a quaternary ammonium ester compound, more preferably a quaternary ammonium ester compound in combination with a silicone.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Liquid compositions according to the present disclosure may include an external structurant. External structurants can provide physical stability to liquid compositions according to the present disclosure, for example by helping to suspend particles. Structurants, when present, are preferably present in an effective amount that is capable of suspending particles in the treatment composition. External structurants may include non-polymeric crystalline, hydroxy-functional structurants and/or polymeric structurants.

Non-polymeric crystalline, hydroxyl functional structurants may comprise a crystallizable glyceride, which may be pre-emulsified to aid dispersion into the final detergent composition. Suitable crystallizable glycerides include hydrogenated castor oil or "HCO" or derivatives thereof, provided that it is capable of crystallizing in the liquid detergent composition.

Polymeric structurants may include naturally derived structurants and/or synthetic structurants. Naturally derived polymeric structurants include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. The structurant may comprise cellulosic fibers, for example in the form of microfibrillated cellulose. Cellulose may be derived from bacterial, wood, or other plants such as fruit or sugar beet.

Synthetic polymeric structurants include: polycarboxylates, polyacrylates, hydrophobically modified ethoxylated urethanes, hydrophobically modified non-ionic polyols and mixtures thereof. The polycarboxylate polymer may be a polyacrylate, polymethacrylate or mixtures thereof. The polyacrylate may be a copolymer of unsaturated mono- or di-carbonic acid and $C_1$-$C_{30}$ alkyl ester of the (meth)acrylic acid. Such copolymers are available from Lubrizol Corp. under the tradename Carbopol® Aqua 30.

The compositions of the present disclosure may include solvent, preferably organic solvent, such as a non-amino-functional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof. Organic solvents can provide physical stability benefits, particularly in compact formulations having relatively low water levels. The compositions of the present disclosure may include from about 5% to about 80%, or from about 10% to about 50%, by weight of the composition, of organic solvent.

Treatment compositions according to the present disclosure may include a perfume delivery system. Suitable perfume delivery systems may include core-shell encapsulates, pro-perfumes (such as amine- and/or silicone-based pro-perfumes), and mixtures thereof. Core-shell encapsulates may comprise a core and a shell surrounding the core. The core may comprise a benefit agent such as perfume, and optionally a partitioning modifier such as isopropyl myristate. The shell may comprise a polymer, for example melamine formaldehyde, polyurea, polyvinyl alcohol, polyacrylate, or a polysaccharide. Encapsulates may comprise a coating that can help with deposition, such as a coating comprising a cationic polymer. Suitable encapsulates may be characterized by a volume-weighted median particle size of from about 10 microns to about 100 microns, or from about 10 microns to about 50 microns, or from about 15 microns to about 40 microns. Perfume delivery systems may provide benefits such as improved perfume stability, deposition, and/or longevity, and may be particularly useful for perfume raw materials that do not associate well with the plant rosin materials of the present disclosure.

The compositions of the present disclosure may include additional aesthetic agents, such as those selected from dyes, opacifiers, pearlescent agents, or mixtures thereof.

Benefit Agent

The processes of the present disclosure relate to benefit agents. The process may comprise the step of combining one or more benefit agents with a base composition. Typically, the one or more benefit agents are combined with the base composition prior to, or at the same time, as when the plant rosin material is combined with the base composition. It is believed that this particular order of addition results in more stable treatment compositions and/or treatment compositions that provide improved performance. For example, the presently disclosed order of addition may lead to improved stability, delivery, and/or performance of the benefit agent on a target surface, such as a fabric or hard surface.

The compositions of the present disclosure may include the benefit agent at a level at which the benefit agent provides its intended benefit when the treatment composition is used as intended. For example, the benefit agent may be added at a level so that the benefit agent is present at a level of from about 0.05% to about 10%, or from about 0.05% to about 5%, or from about 0.1% to about 4%, by weight of the treatment composition.

The benefit agent may be selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, emollients, skin sensates, and mixtures thereof. Particularly preferred benefit agents for the particles include perfume raw materials.

The delivery efficacy of the benefit agent may be most efficacious when the benefit agent is relatively hydrophobic.

The benefit agent may include fragrance material, which may comprise one or more perfume raw materials. The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitrites, and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

Suitable perfume raw materials may include materials such as geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, cinnamaldehyde, anethole, vanillin, ethyl vanillin, eugenol, cinnamon oil, carvone, piperonal, and mixtures thereof. The perfume raw materials may include naturally derived materials, such as essential oils.

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below. A perfume having a variety of PRMs from different quadrants may be desirable, for example, to provide fragrance benefits at different touchpoints during normal usage.

The perfume raw materials may comprise a perfume raw material selected from the group consisting of perfume raw materials having a boiling point (B.P.) lower than about 250° C. and a Log P lower than about 3, perfume raw materials having a B.P. of greater than about 250° C. and a Log P of greater than about 3, perfume raw materials having a B.P. of greater than about 250° C. and a Log P lower than about 3, perfume raw materials having a B.P. lower than about 250° C. and a Log P greater than about 3 and mixtures thereof. Perfume raw materials having a boiling point B.P. lower than about 250° C. and a Log P lower than about 3 are known as Quadrant I perfume raw materials. Quadrant 1 perfume raw materials are preferably limited to less than 30% of the perfume composition. Perfume raw materials having a B.P. of greater than about 250° C. and a Log P of greater than about 3 are known as Quadrant IV perfume raw materials, perfume raw materials having a B.P. of greater than about 250° C. and a Log P lower than about 3 are known as Quadrant II perfume raw materials, perfume raw materials having a B.P. lower than about 250° C. and a Log P greater than about 3 are known as a Quadrant III perfume raw materials. Suitable Quadrant I, II, III and IV perfume raw materials are disclosed in U.S. Pat. No. 6,869,923 Bi.

The treatment composition may comprise fragrance material, where the fragrance material comprises from about 1% to about 40%, by weight of the fragrance material, of Quadrant I perfume raw materials, and/or from about 60% to about 99%, by weight of the fragrance material, of non-Quadrant I perfume raw materials.

The hydrophobic perfume raw materials may be characterized by a relatively high log P value, for example a log P of greater than about 3.0, and may include what is described above as Quadrant III PRMs, Quadrant IV PRMs, or mixtures thereof. The benefit agent may comprise at least about 50%, or at least about 60%, or at least about 70%, or at least about 80%, or at least about 90%, or about 100%, by weight of the benefit agent, of Quadrant III PRMs, Quadrant IV PRMs, or mixtures thereof. Compositions that comprise such levels of Quadrant III and/or IV PRMs as the benefit agent of the particles may be aqueous and comprise at least 60%, or at least 70%, or at least 80%, or at least 90%, or at least 95%, or at least 97%, by weight of the composition, of water, and/or less than 10%, or less than 5%, or less than 3%, surfactant.

Non-limiting examples of Quadrant III PRMs include iso-bornyl acetate, carvacrol, alpha-citronellol, paracymene, dihydro myrcenol, geranyl acetate, d-limonene, linalyl acetate, vertenex, and mixtures thereof.

Non-limiting examples of Quadrant IV (or enduring) PRMs include allyl cyclohexane propionate, ambrettolide, amyl benzoate, amyl cinnamate, amyl cinnamic aldehyde, amyl cinnamic aldehyde dimethyl acetal, iso-amyl salicylate, hydroxycitronellal-methyl anthranilate (known as Aurantiol®), benzophenone, benzyl salicylate, para-tert-butyl cyclohexyl acetate, iso-butyl quinoline, beta-caryophyllene, cadinene, cedrol, cedryl acetate, cedryl formate, cinnamyl cinnamate, cyclohexyl salicylate, cyclamen aldehyde, dihydro isojasmonate, diphenyl methane, diphenyl oxide, dodecalactone, 1-(1,2,3,4,5,6,7,8-octahydro-2,3,8,8-tetramethyl-2-naphthalenyl)-ethanone (known as iso E Super®), ethylene brassylate, methyl phenyl glycidate, ethyl undecylenate, 15-hydroxypentadecanoic acid lactone (known as Exaltolide®), 1,3,4,6,7,8-hexahydro-4,6,6,7,8,8-hexamethyl-cyclopenta-gamma-2-benzopyran (known as Galaxolide®), geranyl anthranilate, geranyl phenyl acetate, hexadecanolide, hexenyl salicylate, hexyl cinnamic aldehyde, hexyl salicylate, alpha-irone, gamma-ionone, gamma-n-methyl ionone, para-tertiary-butyl-alpha-methyl hydrocinnamic aldehyde (known as Lilial®), lilial (p-t-bucinal)®), linalyl benzoate, 2-methoxy naphthalene, methyl dihydrojasmone, musk indanone, musk ketone, musk tibetine, myristicin, oxahexadecanolide-10, oxahexadecanolide-11, patchouli alcohol, 5-acetyl-1,1,2,3,3,6-hexamethylindan (known as Phantolide®), phenyl ethyl benzoate, phenylethylphenylacetate, phenyl heptanol, phenyl hexanol, alpha-santalol, delta-undecalactone, gamma-undecalactone, vetiveryl acetate, yara-yara, ylangene, and mixtures thereof.

Plant Rosin Material

The processes of the present disclosure relate to plant rosin materials. The process may comprise the step of combining a plant rosin material with a base composition. Typically, the plant rosin materials are combined with the base composition at the same time, or after, as when the one or more benefit agents are combined with the base composition.

As used herein, "plant rosin material" may include plant rosins (including resin acids), plant rosin derivatives, or mixtures thereof. Plant rosin material in the present compositions, particles, and processes can provide performance benefits, for example by facilitating improved deposition and/or stability of benefit agents. Such materials may further be preferred to known alternatives in the presently disclosed compositions and processes because they are derived from natural and/or sustainable resources.

As discussed in more detail below, plant rosin is typically derived from conifer plants (class: Pinopsida), usually from pine trees (genus: *Pinus*). Also called "colophony," plant rosin is a solid material produced by heating liquid resins to vaporize the volatile liquid terpene components. Plant rosins are typically composed of resin acids such as abietic acid and related compounds. Plant rosins may be further derivatized, for example through esterification and/or hydrogenation.

The plant rosin materials may be added at any suitable level so as to provide a benefit in the final treatment composition. For example, the plant rosin material may be added in an amount so that it is present at a level of from about from about 0.01% to about 10%, or from about 0.01% to about 5%, or from about 0.05% to about 3%, or from about 0.1% to about 1%, by weight of the final treatment composition. Adding to little may result in little to no added benefit, while adding too much may result in processing challenges.

Plant rosin materials may be characterized by a softening point. Plant rosin materials are typically solid at room temperature, but the softening point is a measure of the glass transition temperature associated with these materials. The softening point of a plant rosin material is determined according to method provided in the Test Method section below.

The plant rosin material may be characterized by a softening point of from about 50° C. to about 175° C., or from about 60° C. to about 150° C., or from about 75° C. to about 125° C. Rosins may need to be softened by heating in order to be incorporated into consumer products. Thus, for ease of processing and/or energy savings, plant rosin materials having relatively lower softening points (e.g., less than 125° C.) may be preferred for the compositions and processes of the present disclosure. Lower softening points may also have an effect on improving the deposition aid performance of the plant rosin material.

Plant rosin materials may be characterized by an acid number (sometimes called "acid value"). The acid number of a plant rosin material relates to the total free acid content of these products. The acid number of a plant rosin material is determined according to method provided in the Test Method section below.

Plant rosin materials may be characterized by an acid number less than about 175, e.g., from about 0 to about 175. For the particles, compositions, and processes of the present disclosure, it may be preferred to use plant rosin material having a relatively low acid number, such as less than about 125, preferably less than about 100, more preferably less than about 75, even more preferably less than about 50, more preferably less than about 25, so as to have minimal effect on the final pH of the treatment composition. Without being bound by theory, it is believed that plant rosin materials having a relatively low acid number may also be more easily dispersible in the base and/or treatment compositions of the present disclosure.

The color of the plant rosin material may be graded based on the Gardner Color standard number, ranging 1 to 18. So as to have minimal effect on the final color of the treatment composition, preferred plant rosin materials of the present disclosure may have a color grade of from about 1 to about 10, preferably from about 1 to about 8. The color grade of a plant rosin material is determined according to method provided in the Test Method section below.

Plant rosin materials may have an odor. Naturally derived resins have an abundance of terpenic compounds. For the compositions and processes of the present disclosure, it may be preferred to select compound with a relatively low amount of terpenic structures and/or odor, so that the naturally derived resin will not interfere with the overall character perception. On the other hand, if there is a desire for a pine-tree-like fragrance character, then the presence of terpenic structures may be preferred.

For example, gum rosins may be preferred over tall oil rosins, as tall oil rosins may include sulfur contaminants that affect the odor. On the other hand, it may be desirable for the plant rosin materials to have a detectable odor, as the "piney" scent associated with rosin material may be useful or desirable in a particular product composition.

Plant rosin materials are typically relatively insoluble in water. For example, plant resin materials according to the present disclosure may be characterized by a solubility of less than 1 g/L, or less than 100 g/L, or less than 1 g/L, or less than 0.1 g/L, or less than about 0.01 g/L, in deionized water at 22° C. Without wishing to be bound by theory, it is believed that the relatively insoluble nature of the plant rosin materials of the present disclosure contribute to the deposition efficiency and performance of the associated benefit agent.

Plant rosin materials may be characterized by a density. Typically, the plant rosin materials are characterized by a density of at greater than 1.0 kg/dm$^3$, preferably at least 1.1 kg/dm$^3$, at 25° C.

Plant rosin materials are typically flammable. For the particles, compositions, and processes of the present disclosure, it may be preferred to use plant rosin materials that have a relatively high flash point, e.g., higher than 190° C., to facilitate easier and safer processing. The flash point of a plant rosin material is determined according to method provided in the Test Method section below.

The processes and compositions of the present disclosure may comprise plant rosin material, where the plant rosin material may comprise a material selected from the group consisting of gum rosin, wood rosin, tall oil rosin, derivatives thereof, and mixtures thereof; preferably gum rosin, derivatives thereof, and mixtures thereof; more preferably a gum rosin ester. The plant rosin material may be a plant rosin ester, preferably an ester formed from an alcohol having two or more carbon atoms, more preferably where the alcohol is glycerol, pentaerythritol, or a mixture thereof. The plant rosin material may be at least partially hydrogenated, preferably fully hydrogenated. The plant rosin material may comprise at least 50%, more preferably at least 60%, more preferably at least 70%, more preferably at least 80%, more preferably at least 85%, by weight of the plant rosin material, of an abietic-type acid, a derivative of an abietic-type acid, or a mixture thereof.

Plant rosins and plant rosin derivatives, as well as premixes comprising such substances, are discussed in more detail below.

A. Plant Rosins

The plant rosin material of the present disclosure may comprise a plant rosin. Plant rosin is typically obtainable from a plant's oleo-resin, which is may be exuded or otherwise derived from a pine tree. The oleo-resin may be distilled to remove volatile terpenes, and the solid material left behind is the plant rosin.

Plant rosin may be solid at room temperature. The solid rosin may be relatively translucent and/or glass-like. The plant rosin material may have a color ranging, for example from faint yellow to a darker brown color, or even black.

Plant rosin is typically a mixture of compounds and is primarily composed of resin acids (also called rosin acids). The plant rosin may comprise at least about 75%, or at least about 80%, or at least about 85%, or at least about 90%, or at least about 95%, by weight of the plant rosin, of resin acids. The plant rosin may comprise from about 75% to about 97%, or from about 80% to about 96%, or from about 85% to about 95%, or from about 90% to about 95%, by weight of the plant rosin, of resin acids. The remaining material may be non-acidic material.

Resin acids are typically monocarboxylic acids having three fused rings. Resin acids may be tricyclic diterpene monocarboxylic acids, for example with a molecular formula of $C_{19}H_{29}COOH$. Resin acids may include abietic-type acids, pimaric-type acids, plicatic acid, or mixtures thereof. The double bonds in abietic-type acids are typically conjugated, whereas the double bonds in pimaric-type acids are not typically conjugated.

Abietic-type acids may include abietic acid, neoabietic acid, dehydroabietic acid, palustric acid, levopimaric acid, or mixtures thereof. Pimaric-type acids may include pimaric acid, isopimaric acid, sandaracopimiaric acid, or mixtures thereof. Structures for these illustrative resin acids are provided below in Table A.

TABLE A

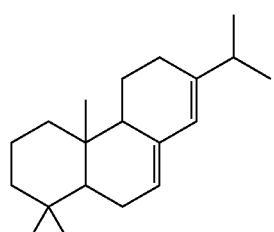
Abietic acid

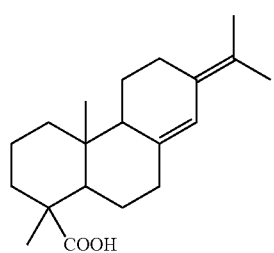
Neoabietic acid

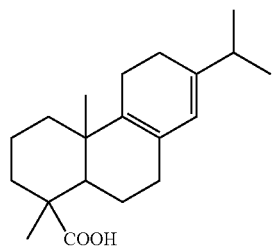
Palustric acid

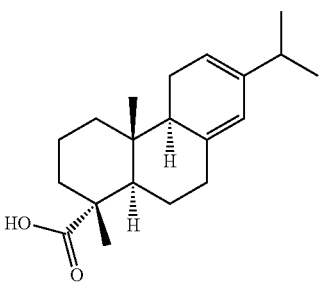
Levopimaric acid

TABLE A-continued

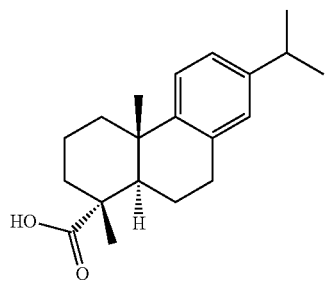
Dehydroabietic acid

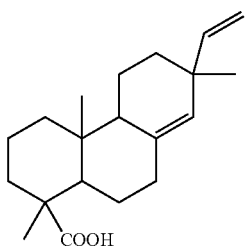
Pimaric acid

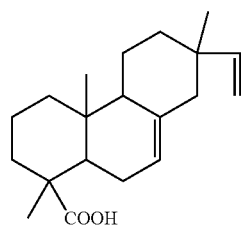
Isopimaric acid

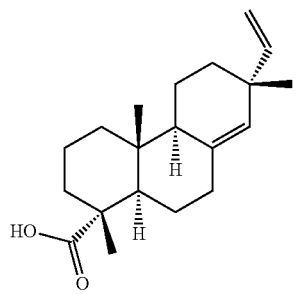
Sandaracopimiaric acid

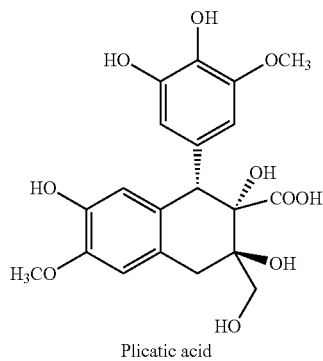 [SMILES: COc1cc2c(cc1O)[C@H](c1cc(O)c(O)c(OC)c1)[C@@](O)(C(=O)O)[C@](O)(CO)C2]
Plicatic acid

The plant rosin may comprise an abietic-type acid, preferably abietic acid. Abietic acid has the empirical formula $C_{19}H_{29}COOH$ and is also known as abietinic acid or sylvic acid. Abietic-type acids are typically the major component of a plant rosin. The plant rosin may comprise at least 50%, or at least 60%, or at least 70%, or at least 80%, or at least 85%, by weight of the plant rosin, of an abietic-type acid, preferably abietic acid.

Plant rosins may be classified depending on the source where it is obtained. For example, plant rosins of the present disclosure may be classified as (and may comprise) gum rosin, wood rosin, tall oil rosin, or a mixture thereof. Gum rosin may be derived from a resin extrudate of a tree or other plant and may be harvested by tapping or wounding the tree and then collecting and processing the extrudate. Wood rosin may be derived from materials that are harvested from pine tree stumps, for example through solvent extraction and/or distillation. Tall oil rosin is a by-product of the distillation of crude tall oil during the Kraft process of wood pulp manufacture when pulping pine trees.

Suitable plant rosins may be obtained, for example, from a variety of pine species, such as *Pinus massoniana* (Masson's pine), *P. elliotti* (slash pine), *P. palustris* (longleaf pine), *P. taeda* (loblolly pine), *P. oocarpa* (Mexican yellow pine), *P. leiophylla* (Chihuahua pine), *P. devoniana* (pino lacio, or Michoacan pine), *P. montezumae* (Montezuma pine), *P. pinaster* (maritime pine), *P. sylvestris* (Scots pine), *P. halepensis* (Aleppo pine), *P. insularis* (Benguet pine), *P. kesiya* (Khasi pine), *P. strobus* (Eastern white pine), or mixtures thereof.

2. Plant Rosin Derivatives

The plant rosin material of the present disclosure may comprise a plant rosin derivative. A plant rosin derivative may be made by chemically modifying a plant rosin material, such as a rosin acid such as abietic acid. Such derivatives may be produced by esterification, hydrogenation, dimerization, polymerization, saponification, or mixtures thereof. Thus, the plant rosin derivative may comprise a rosin ester, a hydrogenated rosin, a hydrogenated rosin ester, a dimerized rosin, a polymerized rosin, or mixtures thereof.

The plant rosin material may be a plant rosin ester. A plant rosin ester may be the reaction product of a plant rosin (e.g., a rosin acid) and an alcohol. A sample condensation reaction between three abietic acid molecules and one glycerol molecule is shown below, resulting in a rosin ester.

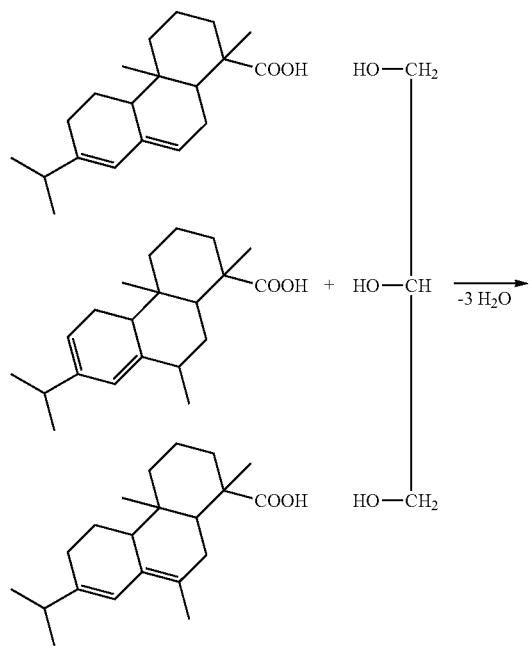

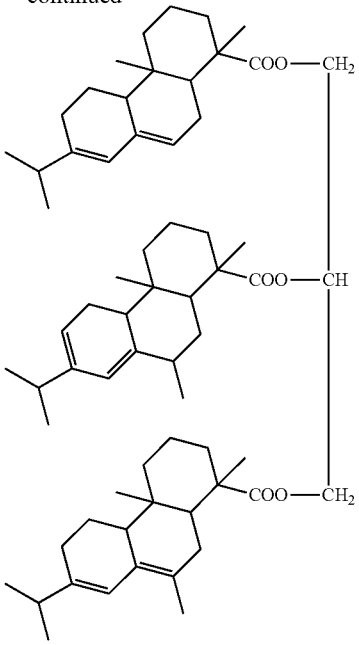

The alcohol in the esterification reaction may be a mono-alcohol, a diol, or a polyol, preferably a diol or a polyol. Suitable mono-alcohols may include methanol, which when reacted with a rosin acid can form a rosin methyl ester. A suitable diol with two hydroxyl groups can include triethylene glycol. The alcohol may be a polyol that comprises three or more hydroxyl groups. Suitable polyols may include a total of three hydroxyl groups (e.g., glycerol), a total of four hydroxyl groups (e.g., pentaerythritol), or a total of six hydroxyl groups (e.g., sorbitol or mannitol). Preferred polyols include glycerol, pentaerythritol, and mixtures thereof.

The alcohol in the esterification reaction may comprise between 1 and 10 carbon atoms, preferably between 1 and 7, more preferably from between 1 and 6, even more preferably between 1 and 5, even more preferably between 3 and 5 carbon atoms. It may be preferred that the alcohol in the esterification reaction comprises at least 2 carbon atoms, preferably from 2 to 10, more preferably from 2 to 6, even more preferably from 2 to 5 carbon atoms. It may be preferred that the rosin ester is not a methyl ester.

The alcohol used in the esterification reaction may have a relatively low molecular weight. For example, the alcohol may have a molecular weight of from about to about 32 daltons to about 300 daltons, preferably from about 32 daltons to about 200 daltons, more preferably from about 32 daltons to about 150 daltons, even more preferably from about 90 daltons to about 150 daltons. Without wishing to be bound by theory, it is believed that a rosin ester formed from a lower-molecular-weight alcohol is likely to be characterized by a relatively lower softening point and/or a lower acid value compared to a rosin ester formed from a relatively higher-molecular-weight alcohol, thereby leading to better processability and/or performance.

The alcohol used in the esterification reaction may be glycerol or pentaerythritol. Thus, the plant rosin derivative may be a glyceryl rosin ester, a pentaerythrityl rosin ester, or a mixture thereof.

The plant rosin derivative may be a hydrogenated rosin. Given that many plant rosin compounds (e.g., rosin acids) are unsaturated, they tend to be oxidatively unstable and may undergo color changes upon storage. Hydrogenation can help to stabilize the rosins and reduce undesirable color change. Furthermore, hydrogenated rosins tend to have lighter colors than the parent rosin, providing more formulation and aesthetic flexibility.

The plant rosins and/or rosin acids may be partially or fully hydrogenated. Below is a sample reaction for the partial and full hydrogenation of abietic acid.

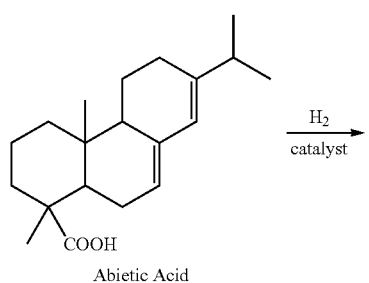
Abietic Acid

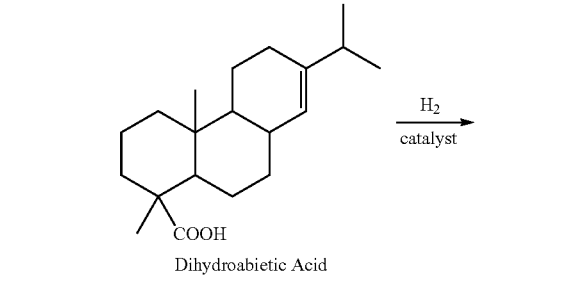
Dihydroabietic Acid

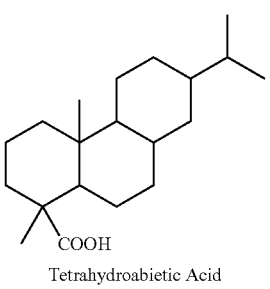
Tetrahydroabietic Acid

The treatment composition may comprise a plant rosin material is at least partially hydrogenated, preferably fully hydrogenated.

The plant rosin derivative may be both hydrogenated and esterified. For example, the plant rosin derivative may be a hydrogenated methyl ester or a hydrogenated glyceryl ester.

The plant rosin derivative may be a dimerized plant rosin. Dimerization may be useful for increasing the softening point and/or stability of a rosin acid. A sample dimerization reaction of abietic acid is shown below.

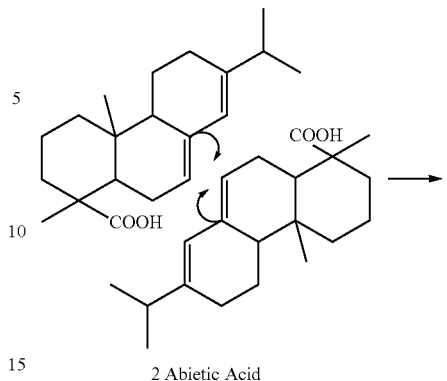
2 Abietic Acid

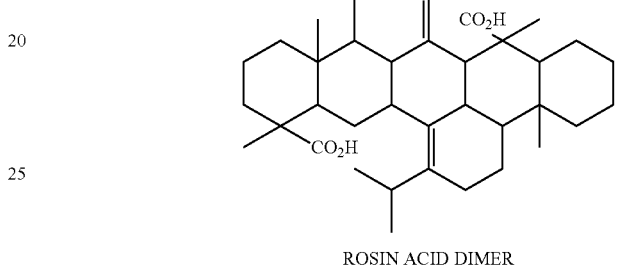
ROSIN ACID DIMER

As it is difficult or even impossible to completely dimerize a sample of rosins, rosin dimers are often present with undimerized rosin acids. Dimerized rosin acids may be further esterified.

A plant rosin derivative may dimerized through ions such as $Zi^{2+}$ or $Ca^{2+}$. For example, zinc resinates are plant rosin derivatives where two abietic acid compounds are bound to a zinc ion.

The plant rosin derivative may be a rosin-based polymer. As used here, in rosin-based polymer is intended to include compounds comprising rosin-based oligomers, including three or more monomeric units derived from rosin acids. The polymer may be a main-chain polymer or a side-chain polymer.

The plant rosin derivative may be a rosin soap, where a rosin acid is reacted with an alkali metal hydroxide (e.g., NaOH or KOH) or an alkaline earth metal hydroxide (e.g., $Ca(OH)_2$). More broadly, the plant rosin derivative may be the salt of a rosin acid.

The plant rosin derivative may be a functionalized plant rosin. In other word, the plant rosin may be functionalized, where one or more functional groups are added to the plant rosin.

A plant rosin derivative may include the product of a Diels-Alder reaction, such as the reaction product of a rosin acid and maleic anhydride; such reaction products may be polymerized.

A plant rosin derivative may include phenolic rosins, where a rosin is reacted with a phenol. A plant rosin derivative may include a rosin alcohol, wherein one or more of the carboxyl groups of the rosin acid are converted to hydroxyl groups.

Commercially available plant rosin derivatives that are suitable for the presently disclosed compositions and processes may include those disclosed in Example 1 of the Examples section below.

Premix Composition

The present disclosure relates to a premix composition, where the premix composition comprises the one or more benefit agents and the plant rosin material. The processes of the present disclosure may include combining the premix composition with the base composition to make the treatment composition.

The one or more benefit agents and the plant rosin material may be pre-combined to form the premix composition. In other words, the process of the present disclosure may comprise the step of providing the premix composition, as is.

The present disclosure may also relate to a process of making a premix composition. In such cases, the process may include the step of combining the one or more benefit agents and the plant rosin material to form a premix. As generally discussed with regard to FIG. 2 above, the premix composition 4 may be pre-made and stored prior to its use, for in the in-line addition process. Alternatively, the premix composition 4 may be made in an in-line process, where the plant rosin material 3 and the one or more benefit agent 2 are combined to form the premix composition 4 substantially immediately prior to combining the premix composition 4 with the base composition 1. In such cases, the components are mixed in a pipe and/or nozzle of the manufacturing system.

In the process of the present disclosure, the plant rosin material and the one or more benefit agents may be added together as a premix composition to the base composition, for example added in a single input stream.

The premix may comprise from about 1% to about 99%, by weight of the premix, of the plant rosin material. The premix may comprise from about 1% to about 99%, by weight of the premix, of the benefit agent. The premix composition may comprise from about 5% to about 95% of the plant rosin material, and from about 5% to about 95% of the one or more benefit agents.

The premix may comprise the plant rosin material and the benefit agent in a weight ratio of from about 1:99 to about 99:1, preferably from about 5:95 to about 95:5, more preferably from about 10:90 to about 90:10, more preferably from about 20:80 to about 80:20, more preferably from about 30:70 to about 80:20, more preferably from about 40:60 to about 80:20. It is believed that the performance benefit increases with higher plant rosin: benefit agent weight ratios.

The premix may comprise an emulsifying agent. The premix may comprise from about 1% to about 95%, or from about 5% to about 95%, preferably from about 5% to about 40% by weight of the premix, of the emulsifying agent. The premix may comprise the plant rosin material and the emulsifying agent in a weight ratio of from about 5:95 to about 95:5. The premix may comprise the benefit agent and the emulsifying agent in a weight ratio of from about 5:95 to about 95:5. Suitable emulsifying agents may include surfactants, amphiphilic polymers, or mixtures thereof. Suitable surfactants may include nonionic surfactants, anionic surfactants, or mixtures thereof, preferably nonionic surfactants.

Suitable nonionic surfactants may include alkoxylated surfactants, pyrrolidone-based surfactants, including alkyl pyrrolidones, alkyl polyglycosides, or mixtures thereof. Preferable HLB value of the nonionic surfactant is from 3 to 12.5.

Suitable alkoxylated nonionic surfactant may include ethoxylated fatty alcohols, which may include linear or branched alkyl chains, preferably $C_6$ to $C_{22}$, preferably $C_8$ to $C_{18}$, more preferably $C_8$ to $C_{12}$ alkyl chains. Suitable alkoxylated nonionic surfactants may include Lutensol™ XP 40 (ex BASF), Lutensol™ XP 70 (ex BASF), Plurafac™ LF 224 (BASF), Plurafac™ LF 401 (BASF), Ecosurf™ EH 9 (DOW), as well as those sold under the Neodol™ and Dobanol™ tradenames (SHELL).

Suitable alkyl pyrrolidones can have the formula:

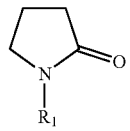

wherein R1 is $C_6$-$C_{20}$ alkyl, or R2NHCOR3, and R2 is $C_1$-6 alkyl and R3 is C6-20 alkyl. R1 is preferably C6-C20 alkyl. Suitable alkyl pyrrolidones may include N-alkyl pyrrolidones, preferably N-alkyl-2-pyrrolidones, more preferably where the alkyl chain is C6 to C20, or C8 to C14, or C12. N-dodecyl-2-pyrrolidone may be particularly preferred, such Surfadone™ LP-300 (ex Ashland).

Suitable alkyl polyglycosides ("APGs") can have the general formula $C_nH_{2n+1}O(C_6H_{10}O_5)_xH$ wherein n is preferably from 9 to 16, more preferably 11 to 14, and x is preferably from 1 to 2, more preferably 1.3 to 1.6. A suitable APG may include Planteren™ APG 600, which is essentially an aqueous dispersion of alkyl polyglycosides wherein n is about 13 and x is about 1.4.

Non-limiting examples of suitable anionic surfactants may include: linear alkyl benzene sulphonate (LAS), alkyl sulphates (AS), alkyl ethoxylated sulphates (AES), laureth sulfates, alkyl ether carboxylates (AEC), and mixtures thereof.

Other suitable surfactants may include rhamnolipids, for example mono-rhamnolipids (such as 3-[3-[(2R,3R,4R,5R,6S)-3,4,5-trihydroxy-6-methyloxan-2-yl]oxydecanoyloxy] decanoic acid) and/or di-rhamnolipids (such as 3-[3-[4,5-dihydroxy-6-methyl-3-(3,4, 5-tri hydroxy-6-m ethyloxan-2-yl)oxyoxan-2-yl]oxyd ecanoyloxy]decanoic acid).

Suitable amphiphilic polymers may include graft copolymers, such as poly(ethylene glycol)-poly(vinyl acetate) graft copolymer, polyvinyl caprolactam-polyvinyl acetate-polyethylene glycol graft copolymer, or mixtures thereof. Commercially available graft copolymers may include Sokalon® HP 22 or Soluplus®, both available from BASF.

The premix may be made by heating the plant rosin material to a temperature equal to or greater than the softening point of the plant rosin material, combining the heated plant rosin material with the benefit agent, and mixing. As an additional or alternative step to heating, the plant rosin material may be grinded to small particles and mixed with the benefit agent. The emulsifying agent, if any, may be added at any suitable point.

The premix may be made by heating the plant rosin material. The plant rosin material may be heated to a temperature equal to or greater than the softening point of the plant rosin material. The premix may be made by combining the heated plant rosin material with the benefit agent, and mixing.

In order to favor the homogeneity of the premix, the mixing may take place in a heated oil bath set at a temperature equal to the softening point of the plant rosin material. As the samples become homogenous, the temperature can be progressively reduced, which helps to lower the risk of loss of volatile materials (e.g., evaporation of volatile PRMs).

A processing aid, for example an emulsifying agent as described above, can be added at any suitable point. Preferably, the emulsifying agent, if any, is combined with the plant rosin material prior to adding the benefit agent (e.g., perfume). It is believed that this order of addition improves the ease of homogenization of the mixture.

As an additional or alternative step to heating, the plant rosin material may be grinded to small particles and mixed with the benefit agent.

Once made, the premix may be stored at ambient temperatures. That being said, when using the premix to make a final product composition, the premix may be heated, for example heated to around 60° C., before being injected in the finished product or otherwise combined with a base composition. This heating step is most likely to be helpful when the premix is characterized by a relatively high rosin:benefit agent (e.g. perfume) weight ratio, such as greater than 50:50. When the premix comprises a nonionic surfactant, for example as an emulsifying agent, the heating step may not be required.

Treatment Composition

The processes of the present disclosure may result in a treatment composition. The treatment compositions may be useful for treating a surface, such as fabric, a hard surface, hair, and/or skin. In addition to the disclosed processes, the present disclosure relates to compositions made by such processes. Such compositions may used in a treatment processes, for example a process where the treatment composition is contacted with a target surface, such as a fabric.

The treatment composition may be a consumer product composition. The consumer product composition may be a fabric care composition, a hard surface cleaner composition, a dish care composition, a hair care composition, a body cleansing composition, or a mixture thereof. The consumer product composition may be a conditioning composition, such as a liquid fabric enhancer composition or a hair conditioner composition.

The treatment compositions of the present disclosure may be fabric care compositions. Such compositions may be used as a pre-laundering treatment, a post-laundering treatment, or may be added during the rinse or wash cycle of the laundering operation. The fabric care composition may be a fabric detergent composition, a fabric conditioning composition, or a mixture thereof, preferably a fabric conditioning composition. Fabric conditioning compositions may include liquid fabric softeners and liquid fabric enhancing compositions.

The treatment composition may be in any suitable form, for example in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof, preferably a liquid.

The treatment composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The treatment composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The treatment composition may be in the form of a unitized dose article, such as a tablet, a pouch, a sheet, or a fibrous article. Unitized dose articles in the form of pouches typically include a water-soluble film, such as a polyvinyl alcohol water-soluble film, that at least partially encapsulates a composition. Suitable films are available from Mono-Sol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The treatment composition may be in the form of a spray and may be dispensed from a bottle, for example, via a trigger sprayer and/or an aerosol container with a valve.

When the treatment composition is a liquid, the composition may be characterized by a viscosity. The composition may have a viscosity of from about 1 to about 1500 centipoises (about 1-1500 mPa*s), from about 50 to about 1000 centipoises (about 50-1000 mPa*s), or from about 100 to 500 centipoises (about 100-500 mPa*s), or from about 100 to about 200 centipoises (about 100-200 mPa*s), at 20 $s^{-1}$ and 21° C., is disclosed. Relatively lower viscosities allow for improved dosing and/or less residue in a dispenser drawer. Viscosity is determined according to the method provided in the Test Methods section below.

The treatment compositions of the present disclosure may be characterized by a pH of from about 2 to about 12, or from about 2 to about 8.5, or from about 2 to about 7, or from about 2 to about 5. The treatment compositions of the present disclosure may have a pH of from about 2 to about 4, preferably a pH of from about 2 to about 3.7, more preferably a pH from about 2 to about 3.5, preferably in the form of an aqueous liquid. It is believed that such pH levels facilitate stability of certain adjuncts, such as conditioning actives (e.g., esterquats). The pH of a composition is determined by dissolving/dispersing the composition in deionized water to form a solution at 10% concentration, at about 20° C.

The treatment compositions, preferably liquid treatment compositions, of the present disclosure may comprise particles. The particles may comprise the plant resin material and the one or more benefit agents, such as perfume raw materials. When the treatment composition is in the form of a liquid, the treatment composition may further comprise a structurant. The process may comprise adding a structurant to the base composition, preferably after the one or more benefit agents and the plant rosin material have been added. The structurant may be present in an effective amount that is capable of suspending the particles in the treatment composition.

The treatment composition may comprise adjunct ingredients, many of which are described above. The adjuncts may added to the base composition before, during, or after the plant rosin material and/or the one or more benefit agents are added to the base composition. For example, neat perfume oil may be added to the base composition prior to a premix composition, where the premix composition comprises the plant rosin material and the one or more benefit agents (e.g., fragrance material). For example, perfume encapsulates may be added after such a premix is added to the base composition. A structurant may be added after the premix composition, and even after perfume encapsulates, if present.

Premix Composition

The present disclosure further relates to a premix composition. The premix composition comprises a plant rosin material and one or more benefit agents. Such premix compositions can be used to make various treatment composition, such as consumer product treatment compositions. Such treatment compositions and related processes are described in more detail above, and the relevant disclosure provided above substantially applies equally to the premix compositions described herein. Still, the premix compositions will be briefly described here.

The premix compositions of the present disclosure are intended to be used as intermediate or feedstock compositions useful in making a final product or treatment composition, rather than be used as final products themselves. The premix compositions may be characterized as having a limited number of ingredients. For example, the premix composition may be comprise no more than five ingredients, or no more than four ingredients, or no more than three ingredients, or no more than two ingredients (e.g., plant rosin material and fragrance material). For the purpose of "counting" ingredients in this manner, "fragrance material" is to be counted as a single material, even if the fragrance material comprises a plurality of perfume raw materials. The premix composition may substantially consist of, or even consist of, the plant rosin material and the one or more benefit agents (e.g., fragrance material), and optionally an emulsifying agent.

Premix compositions according to the present disclosure may be useful in that the premix may be made and then stored until the premix is needed to make the final product/treatment composition. The premix composition may be made at one location and then transported to another, for example by truck or train.

The premix compositions may comprise from about 5% to about 95% of a plant rosin material, and from about 5% to about 95% of one or more benefit agents. The plant rosin material and the one or more benefit agents may be present, in combined total, in the premix composition at a level of from about 30% to about 100%, preferably from about 50% to about 100%, more preferably from about 75% to about 100%, by weight of the premix composition.

The plant rosin material and the one or more benefit agents may be present at a weight ratio of from about 5:95 to about 95:5, preferably from about 20:80 to about 80:20, more preferably from about 30:70 to about 70:30, more preferably from about 40:60 to about 60:40.

Suitable plant rosin materials are described in more detail above. Brief descriptions are provided here, but the descriptions above may substantially apply as well. For example, the plant rosin material of the premix composition may comprise a material selected from the group consisting of gum rosin, wood rosin, tall oil rosin, derivatives thereof, and mixtures thereof, preferably gum rosin, derivatives thereof, and mixtures thereof, more preferably a gum rosin ester. The plant rosin material may be a plant rosin material is a plant rosin ester, preferably an ester of glycerol, pentaerythritol, or a mixture thereof. The plant rosin material is at least partially hydrogenated, preferably fully hydrogenated.

The plant rosin material comprises at least 50%, more preferably at least 60%, more preferably at least 70%, more preferably at least 80%, more preferably at least 85%, by weight of the plant rosin material, of an abietic-type acid.

The plant rosin material may be characterized by one or more of the following characteristics: (a) a softening point of from about 50° C. to about 175° C., or from about 50° C. to about 120° C., preferably from about 60° C. to about 100° C.; and/or (b) an acid value of from about 0 to about 175, or from about 0 to about 100, preferably from about 0 to about 80, more preferably from about 0 to about 60; and/or (c) a color grade of from about 1 to about 10, or from about preferably from about 1 to about 8, more preferably from about 1 to about 6, as graded on the Gardner Color standard number.

The one or more benefit agents may be selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, antioxidants, sanitization agents, disinfecting agents, germ control agents, mold control agents, mildew control agents, antiviral agents, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antibacterial actives, antiperspirant actives, emollients, anti-microbial and anti-fungal actives, skin sensates, and mixtures thereof. Particularly preferred benefit agents for the particles include perfume raw materials, anti-microbial actives, anti-fungal actives, or mixtures thereof, more preferably fragrance materials/perfume raw materials.

The one or more benefit agent may be a fragrance material. The fragrance material may comprise from about 1% to about 40%, by weight of the fragrance material, of Quadrant I perfume raw materials, and/or from about 60% to about 99%, by weight of the fragrance material, of non-Quadrant I perfume raw materials.

The premix composition may further comprise an emulsifying agent, preferably selected from a surfactant, an amphiphilic polymer, or a mixture thereof. The premix composition may comprise an amphiphilic polymer, preferably an amphiphilic graft co-polymer, more preferably an amphiphilic graft co-polymer comprising a polyalkylene glycol as a graft base and one or more side chains, the side chains comprising vinyl acetate moieties and optional N-vinylcaprolactam moieties.

The premix composition may be a liquid. The premix composition may comprise less than 5%, by weight of the premix composition, of water.

It may be preferred that the premix composition has a relatively low viscosity, making them relatively easier to homogenize in the finished product without additional heating. The premix composition may be characterized by a viscosity of from about 0.01 to about 25 Pa·s, or preferably from about 0.01 to about 20 Pa·s, or more preferably from about 0.02 to about 15 Pa·s, at 40° C. at a shear rate of 11.71 $s^{-1}$.

The present disclosure further relates to processes of making premix compositions as described herein. For example, such processes may include the step of combining a plant resin material and one or more benefit agents, and optionally an emulsifying agent.

To make the premix composition, the plant resin material may be provided as small particles to facilitate homogenization of the premix. If the plant resin material is provided a solids that are larger than desired, the process may include grinding or pulverizing the plant resin material into smaller particles. In a bench top operation, this may be accomplished with a mortar and pestle.

The process of making a premix composition may include providing plant resin material, adding the one or more benefit agents, and mixing. The mixture may be mixed, for example, for a period of from one hour to four hours, preferably from about two hours to about three hours.

The plant resin material may be provided at room temperature (e.g., 20-22° C.). The mixture of plant resin material and the one or more benefit agents may be heated prior to mixing, which can improve ease of homogenization. The mixture may be heated to a temperature up to the softening point of the plant resin material, preferably to less than the softening point of the plant resin material, more preferably to a temperature of from about 40° C. to about 60° C., more preferably to a temperature of from about 40° C. to about 50° C. It is preferred that the temperature is not too high, so as to avoid evaporation of volatile benefit agents, particularly fragrance material. The mixture may be mixed at the elevated temperature for a period of from one hour to four hours, preferably from about two hours to about three hours. After the mixture has been substantially homogenized, the mixture may be cooled to ambient temperature. If the viscosity of the premix at ambient temperature is lower than 6000 cP, then the heating step may not be needed.

If an emulsifying agent it used, it may be added at any suitable point. Preferably, the plant resin material and the emulsifying agent are combined prior to the addition of the one or more benefit agent (e.g., fragrance material). Use of an emulsifying agent may be preferred to help with homogenization of the premix composition, and may even make the step of heating the mixture less necessary, thereby saving energy, particularly when the emulsifying agent is a nonionic surfactant. The weight ratio of plant resin material to emulsifying agent to benefit agent (preferably fragrance material) in the premix composition may be 25/25/50, or 35/25/40, or 45/15/40, or 30/20/50, or 40/10/50, preferably 25/25/50 or 35/25/40, which is preferably the entirety of the premix (e.g., 100 wt %).

As described in more detail above, the premix composition may be useful in processes of making a treatment composition. As such, the present disclosure further relates to a process of making a treatment composition, where the process comprises the step of combining a premix composition as described herein and a base composition as described herein. The premix composition may be provided to or otherwise added to the base composition. Other adjunct materials may be added before, during, or after the addition of the premix composition. The premix may be heated to a temperature above ambient temperature, for example to a temperature of from about 40° C. to about 75° C., preferably from about 50° C. to about 60° C., and added to the base composition. When the premix composition comprises an emulsifying agent, it may not be necessary to heat the premix prior to adding to the base composition.

The mixture of the premix composition and the base composition may need to be mixed at relatively high shear to ensure suitable incorporation/homogenization of the premix into the base composition.

COMBINATIONS

Specifically contemplated combinations of the disclosure are herein described in the following lettered paragraphs. These combinations are intended to be illustrative in nature and are not intended to be limiting.

A. A process of making a treatment composition, the process comprising the steps of: providing a base composition, wherein the base composition comprises an adjunct material; and adding a plant rosin material and one or more benefit agents to the base composition, wherein the plant rosin material is added with or after the one or more benefit agents.

B. The process according to paragraph A, wherein the plant rosin material is added with the one or more benefit agents.

C. The process according to paragraph B, wherein the plant rosin material and the one or more benefit agents are added in a single input stream as a premix composition to the base composition.

D. The process according to paragraph C, wherein the premix composition comprises: from about 5% to about 95% of the plant rosin material, and from about 5% to about 95% of the one or more benefit agents.

E. The process according any of paragraphs C or D, wherein the premix composition further comprises an emulsifying agent, preferably an emulsifying agent selected from a surfactant, an amphiphilic polymer, or a mixture thereof.

F. The process according to paragraph A, wherein the plant rosin material is added to the base composition after the one or more benefit agents are added to the base composition.

G. The process according to any of paragraphs A-F, wherein the plant rosin material and the one or more benefit agents are present in the treatment composition at a weight ratio of from about 5:95 to about 95:5, preferably from about 20:80 to about 80:20, more preferably from about 30:70 to about 70:30, more preferably from about 40:60 to about 60:40.

H. The process according to any preceding cl according to any of paragraphs A-G, wherein the process further comprises heating the plant rosin material above ambient temperature prior to combining the plant rosin material with the one or more benefit agent, with the base composition, or both, preferably heating the plant rosin material at least to the softening point of the plant rosin material.

I. The process according to any of paragraphs A-G, wherein the process further comprising the step of combining the plant rosin material and the one or more benefit agents at ambient temperature, preferably a temperature of from about 18° C. to about 25° C., more preferably from about 18° C. to about 22° C., wherein the weight ratio of plant rosin material to benefit agent is less than 50:50, preferably less than 40:60, more preferably less than 30:70, more preferably less than 20:80, or even less than 10:90, preferably wherein the one or more benefit agents comprises perfume raw materials.

J. The process according to any of paragraphs A-I, wherein the plant rosin material is provided as a powder characterized by particles having an average diameter of less than 5 mm, or less than 3 mm, or less than 2 mm, or less than 1 mm, or from about 10 μm to about 500 um, optionally wherein the process further comprises the step of grinding or pulverizing larger pieces of the plant rosin materials to form the powder.

K. The process according to any of paragraphs A-J, wherein the plant rosin material comprises a material selected from the group consisting of gum rosin, wood rosin, tall oil rosin, derivatives thereof, and mixtures thereof, preferably gum rosin, derivatives thereof, and mixtures thereof, more preferably a gum rosin ester.

L. The process according to any of paragraphs A-K, wherein the plant rosin material is characterized by one or more of the following characteristics: (a) a softening point of from about 50° C. to about 175° C., or from about 50° C. to about 120° C., preferably from about 60° C. to about 100° C.; and/or (b) an acid number of from about 0 to about 175, preferably from about 0 to about 100, preferably from about 0 to about 80, more preferably from about 0 to about 60, more preferably from about 0 to about 40, even more preferably from about 0 to about 20; and/or (c) a color grade of from about 1 to about 10, or from about preferably from about 1 to about 8, more preferably from about 1 to about 6, as graded on the Gardner Color standard number.

M. The process according to any of paragraphs A-L, wherein the one or more benefit agents comprises a fragrance material.

N. The process according to any of paragraphs A-M, wherein the base composition is a liquid.

O. The process according to any of paragraphs A-N, wherein the base composition comprises at least 8% water, preferably at least 25% water, more preferably at least 50% water, more preferably at least 60% water, more preferably at least 70% water, more preferably at least 75% water, more preferably at least 80% water, more preferably at least 90% water, by weight of the base composition.

P. The process according to any of paragraphs A-O, wherein the adjunct ingredient comprises a surfactant system, fabric softening agents, or combinations thereof, (a) preferably wherein the surfactant system comprises anionic surfactant, nonionic surfactant, cationic surfactant, and/or zwitterionic surfactant, and/or (b) preferably wherein the fabric softening agents comprise a quaternary ammonium compound, silicone compounds, or both.

Q. The process according to any of paragraphs A-P, wherein the plant rosin material and the one or more benefit agents are combined with the base composition via a batch process, via a continuous-loop addition process, or via an in-line addition process, preferably via an in-line process.

R. The process according to any of paragraphs A-Q, wherein the plant rosin material and the one or more benefit agents are combined with the base composition via an in-line process and mixed with a dynamic mixer, preferably a rotator-stator mixer, characterized by a tangential velocity of from about 7 m/s to about 19 m/s, preferably from about 12 m/s to about 16 m/s, more preferably about 14 m/s.

S. The process according to any of paragraphs A-R, wherein the treatment composition made from the process comprises particles, wherein the particles comprise the plant resin material and the one or more benefit agents.

T. The process according to any of paragraphs A-S, wherein the treatment composition is a liquid, and wherein the treatment composition further comprises adding a structuring agent, preferably present in an effective amount that is capable of suspending the particles in the treatment composition.

U. The process according to any of paragraphs A-T, wherein the treatment composition is a consumer product composition, preferably a fabric care composition, a hard surface cleaner composition, a dish care composition, a hair care composition, a body cleansing composition, or a mixture thereof, preferably wherein the fabric care composition is a fabric detergent composition, a fabric conditioning composition, or a mixture thereof.

V. The process according to any of paragraphs A-U, wherein the treatment composition is a liquid.

W. A treatment composition made according to the process of any of paragraphs A-V.

X. A premix composition comprising: from about 5% to about 95% of a plant rosin material, and from about 5% to about 95% of one or more benefit agents, preferably wherein the one or more benefit agents comprises fragrance material, wherein the plant rosin material and the one or more benefit agents are present in total in the premix composition at a level of from about 30% to about 100%, preferably from about 50% to about 100%, more preferably from about 75% to about 100%, by weight of the premix composition.

Y. The premix composition according to paragraph X, wherein the premix composition further comprises an emulsifying agent, preferably an emulsifying agent selected from a surfactant, an amphiphilic polymer, or a mixture thereof, wherein if the emulsifying agent comprises a surfactant, the surfactant preferably comprises a nonionic surfactant, more preferably a nonionic surfactant selected from the group consisting of alkoxylated surfactants, pyrrolidone-based surfactants, alkyl polyglycosides, and mixtures thereof, and wherein if the emulsifying agent comprises an amphiphilic polymer, the amphiphilic polymer preferably comprises a graft copolymer, more preferably a graft copolymer selected from the group consisting of poly(ethylene glycol)-poly (vinyl acetate) graft copolymer, polyvinyl caprolactam-polyvinyl acetate-polyethylene glycol graft copolymer, and mixtures thereof.

Z. The premix composition according to any of paragraphs X-Y, wherein the premix composition is characterized by a viscosity of from about 0.01 to about 25 Pa·s, or preferably from about 0.01 to about 20 Pa·s, or more preferably from about 0.02 to about 15 Pa·s, at 40° C. at a shear rate of 11.71 s$^{-1}$.

AA. The premix composition according to any of paragraphs X-Z, wherein the premix composition comprises less than 5%, by weight of the premix composition, of water.

TEST METHODS

It is understood that the test methods that are disclosed in the Test Methods Section of the present application should be used to determine the respective values of the parameters of Applicant's claimed subject matter as claimed and described herein, unless indicated otherwise.

Test Method for Determining the Logarithm of the Octanol/Water Partition Coefficient (Log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Softening Point Test Method

If available, the softening point of a plant rosin material as provided by the manufacturer/supplier is to be used.

If not available from the manufacturer/supplier, the softening point is determined according to ASTM E28-18, "Standard Test Methods for Softening Point of Resins Derived from Pine Chemicals," using the version approved Jul. 1, 2018, and published July 2018. More specifically, the Reference Method ("Automated Ring and Ball Softening Point Method") provided therein is to be followed. The method is summarized here.

As used herein (and as described in ASTM E28-18), the softening point is defined as the temperature at which a disk of the sample held with a horizontal ring (brass shouldered ring; 19.8 mm inner ring diameter, 23.0 outer diameter, as indicated in the ASTM method) is forced downward a distance of 25.4 mm (1 in.) under the weight of a steel ball (9.53 mm diameter; mass between 3.45 and 3.55 g) as the sample is heated at 5 C/min in a water, glycerin, silicone oil, ethylene glycol/water, or glycerin/water bath.

Sample Preparation: Select a representative sample of the rosin material to be tested. The sample should include flakes, pastilles, or freshly broken lumps free of oxidized surfaces; avoid inclusion of finely divided material or dust. Melt the sample in a clean container; avoid overheating, and avoid incorporating air bubbles into the sample. The time from the beginning of heating to the pouring of the sample should not exceed 15 minutes. Rest the ring, bottom down, on a metal surface; the ring may be preheated. Pour the melted rosin sample into the ring so as to leave an excess upon cooling. After cooling for at least 30 minutes, remove excess material from the periphery and top of the ring.

Bath Liquid: The selection of the bath liquid will depend on the softening point ("SP") of the rosin material. For SPs between 35 C and 80 C, use water (distilled or deionized, freshly boiled). For SPs between 80 C and 150 C, use USP Glycerin. For SPs above 80 C, use Silicone Oil (Polydimethylsiloxane—200 fluid, 50 cSt, from Dow Corning, Midland, MI). For SPs up to 35 C, use a 50/50 (v/v) mixture of Ethylene Glycol and Distilled Water; the bath should be cooled to −25 C in a precooled freezer or an isopropyl dry-ice bath.

Test: Use a suitable automated ring and ball-softening point instrument with control unit; calibrate according to the manufacturer's instructions. Provide a stir bar to a 600 mL beaker and fill with a bath liquid as provided above, depending on the softening point of the rosin material. Set up the apparatus, ring, ball, test insert, support pins as recommended by the manufacturer's instructions. Verify that the control unit is set for the correct bath liquid.

Heat the bath so that the temperature of the bath liquid is raised uniformly at a rate of 5 C/min. The test is complete when then light beam has been interrupted by the falling ball and material. Record the softening point at the temperature displayed on the unit after the test is completed.

Acid Number Test Method

If available, the acid number of a plant rosin material as provided by the manufacturer/supplier is to be used.

If not available from the manufacturer/supplier, the acid value is determined according to ASTM D465-15 (Reapproved 2020), "Standard Test Methods for Acid Number of Pine Chemical Products Including Tall Oil and Other Related Products," as approved Jun. 1, 2020 and published June, 2020. More specifically, the Referee Method ("Potentiometric Method") provided therein is to be followed. The method is summarized here.

Provide freshly chipped samples of rosin material, which may be further crushed to facilitate weighing and dissolution; pieces with oxidized surfaces, as well as existing rosin dust or powder, should not be used. If a nonhomogenous liquid, place in a closed container with a capillary vent or its equivalent, and heat in a hot water bath; the sample may be agitated during heat, and used after homogenous and well stirred.

Based on the following table, transfer the proscribed amount of sample to a 400 mL tall-form beaker; add the proper amount of solvent I and swirl to dissolve, heating gently if necessary. Add the proper amount of solvent II, if required, and cool to near room temperature. Immerse each electrode of a glass electrode pH meter (calibrated/standardized according to the manufacturer's instructions) in the solution. Stir with a stir bar.

Titrate with a standard alkali solution (a 0.5 N or 0.1 N KOH solution), recording the buret and pH meter readings. Sufficient alkali may be added to bring the pH of the solution to about 8. Add alkali in 1.0 mL portions until the change in pH per increment added amounts to about 0.3 pH unit. Reduct the additions of alkali to 0.1 mL or smaller until the end point has been passed, as indicated by a significant decrease in pH units er 0.1 mL added. Continue the titration with 1.0 mL portions until it becomes apparent that the inflection point has been well defined.

Determine the inflection point (point of maximum change in pH per mL of alkali solution) to the nearest 0.05 mL by plotting the pH readings against the milliliters of alkali used. (For greater accuracy, the chance in pH per mL may be plotted against the pH; the peak corresponds to the inflection point.) The inflection point is considered the end point of the titration.

The acid number of the sample, expressed as milligrams of KOH per gram of sample is calculated as follows, and may be reported to the nearest whole number:

$$\text{Acid Number} = (A \times N \times 56.1)/B$$

where: A=alkali solution (in mL) required for titration of the specimen; N=normality of the alkali solution, and B=specimen weight (in grams).

Color Grade Test Method (Gardner Color)

If available, the color grade (Gardner color) of a plant rosin as provided by the manufacturer/supplier is to be used.

If not available from the manufacturer/supplier, the color grade (Gardner color) is determined according to ASTM D6166-12 (Reapproved 2016), "Standard Test Method for Color of Pine Chemicals and Related Products (Instrumental Determination of Gardner Color)," as approved Dec. 1, 2016, and published December, 2016. The method is summarized here.

The color of a liquid sample is measured using an instrument, such as a Gardner Color Comparator L, 115V (ex. BYK), capable of measuring transmitted color and reporting in Gardner colors (or, less preferred, in a color system that can be converted to Gardner colors by known methods, such as those disclosed in the ASTM D6166-12). The instrument is calibrated according to the manufacturer's instructions.

To prepare the rosin sample for color analysis, a molten sample of the rosin material is introduced to a glass cuvet (10-mm path, unless a different path length is specified by the instrument manufacturer). If the sample is solid, it should comprise freshly broken lumps and be free of dust and finely divided material; the solid should be melted (e.g. in 15 minutes or less, in an oven, sand bath, or oil bath), taking care to avoid overheating and introduction of bubbles. After the molten sample is introduced to the glass cuvet, measurements should be taken while still molten. If the material is cloudy, it should be filtered.

The glass cuvet is inserted into the instrument, and the color is measured by following the manufacturer's instructions.

Flash Point Test Method

If available, the flash point of a plant rosin as provided by the manufacturer/supplier is to be used.

If not available from the manufacturer/supplier, the flash point is determined according to ASTM D92-18, "Standard Test Methods for Flash and Fire Points by Cleveland Open Cup Tester," as approved Jul. 1, 2018, and published July, 2018.

Test Method for Determining Amounts of Major Rosin Acid Isomers

If available, the amounts of the major rosin acid isomers of a plant rosin as provided by the manufacturer/supplier is to be used.

If not available from the manufacturer/supplier, the amounts of the major rosin acid isomers are determined according to ASTM D5974-15, "Standard Test Method for Fatty and Rosin Acids in Tall Oil Fractionation Products by Capillary Gas Chromatography," as approved Jul. 1, 2015, and published August, 2015. The method is summarized here.

This method uses gas chromatography to determine the levels of, for example, rosin acids present in a rosin sample. Prior to chromatographic separation, certain free acids should be converted to more volatile and more stable methyl esters. For rosin acids, this conversion may take place by means of tetramethylammonium hydroxide (TMAH).

To prepare the methyl ester, a rosin sample (if solid, freshly broken to avoid oxidation) is dissolved in 0.5-3.0 mL of a 50:50 ether/methanol mixture (and optionally 2 to 3 drops of toluene), 2 to 3 drops of phenolphthalein indicator solution is added. The mixture is titrated to a pH of 7.9 to 8.1, or to the very first permanent pink color, with a 6% solution of TMAH. If over-titrated, the mixture may be back-titrated with a 5% acetic acid solution (v/v) in methanol. When the solution is injected into the heated injection port of the chromatograph, the tetramethylammonium salts are pyrolyzed to methyl esters.

A gas chromatograph (GC) equipped with a flame ionization detector (FID) is used and operated under the following conditions: Column temperature (oven temperature)—initial, 150 C; hold, 5 min.; ramp, 5 C/min; final 250 C; hold 10 min; injection port temp., 300 C; injection port liner, glass split; detector temp., 325 C; carrier gas, helium; linear gas velocity, 19.5-20.5 cm/s; split ratio, 100 to 1 maximum; detector, FID; hydrogen, 30 mL/min; air, 400 mL/min; makeup gas, 30 mL/min. A high resolution column, preferably 30 m in length, 0.32 mm internal diameter, with a 0.20-μm film thickness of bicyanopropylsiloxane-type liquid, is used.

Prepare calibration standards of myristic acid and high-purity standards of rosin acids that are expected to be present, record the weights, and convert to methyl esters as described above. To prepare the test sample, accurately weigh about 50 mg of sample and about 15 mg of myristic acid in a suitable vial, record the weight, and convert to methyl esters as described above.

Use the calibration standards (injecting 0.5-1.0 μL) to calibrate the GC, recording the retention times and calculating the individual relative response factors. To analyze the test sample, inject 0.5-1.0 μL (diluting the sample with additional solvent if necessary), obtain the peak areas of all of the peaks needed from the chromatogram, and calculate the absolute value of each peak of interest. The relative percent of each rosin acid methyl ester present may be determined by dividing the peak area for the rosin acid methyl ester being determined by the sum of areas of all rosin acid methyl ester peaks.

Fabric Treatment Method

When treating fabrics with a composition according to the present disclosure in the experiments below, the following method is followed unless otherwise indicated. For each treatment, a washing machine (ex Miele) is loaded with about 3 kg of a fabric load. The fabric load comprises about 1065 g knitted cotton fabric and about 1065 g polyester-cotton fabrics (50/50). Additionally, the fabric load comprises twenty terry towel tracers, which weigh together about 870 g. Then one washing cycle is run at 95° C.

Prior to the test treatment, the load is preconditioned twice, each time using the 95° C. short cotton cycle with 79 g of unperfumed IEC A Base detergent (ex WFK Testgewebe GmbH), followed by two additional 95° C. washes without detergent.

For the test treatment, the load is washed using a 40° C. short cotton cycle, 1200 rpm spin speed with 79 g IEC A Base detergent, which is added at the start of the wash cycle in the appropriate dispenser. A dosage of 40 ml of the test fabric treatment composition is added in the appropriate dispenser.

Method to Determine Headspace Concentration Above Treated Fabrics

The fabric tracers from the abovementioned Fabric Treatment method may beanalyzed via headspace analysis at at least two specific touchpoints:

WFO (Wet Fabric Odor, or WET): Wet fabrics are analyzed after the fabric treatment method is finished.

DFO (Dry Fabric Odor, or DRY): Dried Fabrics are analyzed after the fabrics have been line-dried in a closed room for approximately twenty-four hours.

The headspace above the cotton terry tracers is analyzed using SPME headspace GC/MS (gas chromatography mass spectrometry) approach. 4 cm×4 cm aliquots of cotton tracers are transferred to 25 ml headspace vials. The fabric samples are equilibrated for 10 minutes at 65° C. The headspace above the fabrics is sampled via SPME (50/30 μm DVB/Carboxen/PDMS) for 5 minutes. The SPME fiber is subsequently on-line thermally desorbed into the GC. The analytes are analyzed by GC/MS in full scan mode. The total perfume HS response and perfume headspace composition above the tested legs can be determined.

Viscosity Method

Viscosity of a liquid composition is measured using a DV-E viscometer from Brookfield. The spindle is automatically spun at a rate of 60 rpm until a stable value is given in centipoise (cP).

Viscosity of the premix comprising rosin plant, delivery agent and potentially emulsifying agent is measured using a HAAKE MARS from Thermo Scientific using a 60 mm 1° cone and a gap size of 52 micrometers. The shear viscosity at $20\ s^{-1}$ can be obtained from a logarithmic shear rate sweep from $0.01\ s^{-1}$ to $1200\ s^{-1}$ at 21° C. The viscosity may be expressed as centipoise (cP).

Particle Size—Image Analysis

Depending on the relative size of the particle, one of two methods is employed: image analysis if the approximate volume-weighted median particle size of the population is 10 μm or greater, or microscopy if the approximate volume-weighted median particle size of the population is less than 10 m. These methods are described in more detail below.

A. Image Analysis

The volume weighted median particle size distribution is calculated from images taken from the sample flowing through a variable size flow cell. This instrument is specifically designed for image analysis device for liquid applications (Occhio FC200S). The sample is pumped via a syringe pump at very low speed through the flow cell, while the sample passes through the flow cell images are taken at set times. The speed is matched with the frame speed of the camera and it is dependent on the behaviour of the sample and the particles it contains. The flow cell sizes used were 250 and 500 μm and were depending on the size of the capsules. Detection of the capsules is done via grayscale threshold. Callisto version 2013.13 software is used to read out the pixels and calculate size and shape parameters. The size descriptor used is ISO area diameter.

Illumination is a red-led light source, adjustment of illumination is done manually until proper grayscale detection of the particles is possible. Hardware magnification is dependent on the size of the particles: 6× or 9×.

B. Microscopy

The volume-weighted average median particle size of the particles is calculated from the values obtained by microscopically observing and measuring the diameter of around 900 capsules observed in randomly sampled aliquots. The microscope used is the Leica DM6000B. The magnification of the microscope is set to 200×. The outputs obtained after the microscopy analysis are: (1) list of diameters detected; and (2) counts per each diameter size detected.

Therefore, the volume (V) of each particle is calculated with the following equation:

$$V = 4/3 \pi r^3$$

where r is the radius of each detected particle. Finally, the volume-weighted median particle size is calculated (e.g., via a spreadsheet, such those created in Microsoft Excel™), assuming that each particle is a sphere.

EXAMPLES

The examples provided below are intended to be illustrative in nature and are not intended to be limiting.

Example 1. Exemplary Plant Rosin Materials

Table 1 shows a variety of commercially available plant rosin materials. Additional information is provided where available.

Example 2. Order of Addition (Plant Rosin Vs. Perfume)

This example relates to various liquid fabric enhancer ("LFE") products made using different orders-of-addition with regard to the plant rosin material and the benefit agent (i.e., fragrance material/perfume). The materials are added to the LFE composition, which is reported in Table 2 A.

TABLE 2A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])

In Sample 1, the plant rosin material and the perfume are added simultaneously as a premix composition. In Sample 2, the materials are added as separate inputs, with the perfume being added first and the plant rosin material being added second. In Sample 3, the materials are added as separate inputs, with the plant rosin being added first and the perfume being added second. The weight percentages provided below are by weight of the finished product.

TABLE 1

Exemplary plant rosin materials

| No. | Rosin Type | Derivative Type | Additives | Softening Point (° C.) | Acid Value (mg KOH/g) | TRADE NAME | Mfr.* |
|---|---|---|---|---|---|---|---|
| 1 | Gum Rosin | — | — | 79 | 163 | — | A |
| 2 | Gum Rosin | Glycerol ester | — | 88 | 8 | Permalyn 5095 | B |
| 3 | Gum Rosin | Pentaerythritol ester | — | 125 | 13 | Lurefor 125 | A |
| 4 | Gum Rosin | Pentaerythritol ester | — | 100 | 15 | Permalyn 5110 | B |
| 5 | Gum Rosin | Methyl ester | — | — | 5 | Abalyn D-E | C |
| 6 | Gum Rosin | Hydrogenated | — | 70 | 158 | Staybelite Resin-E | C |
| 7 | Misc. Rosin | Partially Hydrogenated | — | 75 | 168 | Foralyn E | C |
| 8 | Gum Rosin | Partially dimerized | — | 103 | 146 | Poly-Pale | C |
| 9 | Wood Rosin | Hydrogenated glycerol ester | — | 84 | 6 | Foral 85 | B |
| 10 | Wood Rosin | Hydrogenated pentaerythritol ester | — | 99 | 11 | Foral 105 | B |
| 11 | Tall Oil | Saponified sodium soap | — | — | 0.5 | Dresinate TX Rosin Soap | C |
| 12 | Misc. Rosin | Dimerized; Zinc resinate | Zinc salt | 160 | 5 | Zincogral Z | B |

* Mfr. = Manufacturer, according to the following key:
A—Luresa Resinas S. L.
B—DRT
C—Eastman

TABLE 2B

| Sample # | Plant Rosin Material Trade Name | Wt % | Benefit Agent Type | Wt % | Order of addition to make finished product |
|---|---|---|---|---|---|
| 1 | Permalyn 5095 | 1.2% | Perfume | 0.5% | Simultaneous (as plant rosin/perfume premix) |
| 2 | Permalyn 5095 | 1.2% | Perfume | 0.5% | Perfume first; plant rosin second |
| 3 | Permalyn 5095 | 1.2% | Perfume | 0.5% | Plant rosin first; perfume second |

For each leg, a parallel product is made that only adds the perfume (no plant rosin material). Additionally, for each product, a structuring agent (FLOSOFT™ FS 222, ex SNF Floerger®) is added as last step at a weight concentration of 0.2% in the finished product. The products are used to treat fabrics according to the method provided above, and the dry fabric odor (DFO) for each is measured. The results are provided in Table 2C below. Additionally, Table 2C shows the "Delta DFO," showing the difference between the DFO scores for the products of Table 2B ("plant rosin+perfume") and the products that only include the perfume ("perfume only"). Furthermore, the "DFO Ratio" is the ratio of the two DFO scores in that leg. Relatively higher Delta DFO scores and DFO Ratios indicate that the formulations comprising the plant rosin are providing freshness benefits compared to perfume-only formulations.

TABLE 2C

| Sample # | DFO Headspace (nM/L) (perfume + plant rosin) | DFO Headspace (nM/L) (perfume only) | Delta DFO | DFO Ratio |
|---|---|---|---|---|
| 1 | 130 | 2.82 | +127.2 | 46.1 |
| 2 | 85.3 | 2.82 | +82.5 | 30.2 |
| 3 | 40 | 2.82 | +37.2 | 14.2 |

Additionally, Table 2D shows the "Delta WFO," showing the difference between the WFO scores for the products of Table 2B ("plant rosin+perfume") and the products that only include the perfume ("perfume only"). Furthermore, the "WFO Ratio" is the ratio of the two WFO scores in that leg. Relatively higher Delta WFO scores and WFO Ratios indicate that the formulations comprising the plant rosin are providing freshness benefit compared to perfume-only formulations.

TABLE 2D

| Sample # | WFO Headspace (nM/L) (perfume + plant rosin) | WFO Headspace (nM/L) (perfume only) | Delta WFO | WFO Ratio |
|---|---|---|---|---|
| 1 | 536 | 235 | +301.0 | 2.3 |
| 2 | 526 | 235 | +291.0 | 2.2 |
| 3 | 416 | 235 | +181.0 | 1.8 |

Furthermore, the results provided in Tables 2C and 2D indicate that products made with the order-of-addition of Sample 1 (e.g., a premix) provide the best freshness at the DFO and WFO touchpoints, followed by the order-of-addition of Sample 2 (perfume first, plant rosin second).

Example 3. Ratios of Plant Rosin and Benefit Agent

A liquid fabric (LFE) base composition according to Table 3A, below, is provided.

TABLE 3A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Structuring agent[2] | 0.2% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])
[2]FLOSOFT ™ FS 222, ex SNF Floerger ®

The following rosin/perfume premixes are prepared, as shown in Table 3B. The weight percentages are based on weight of the premix composition.

The premixes are provided at levels that provide the same total perfume to a liquid fabric enhancer (LFE) base composition, and the resulting liquid conditioning product is used to treat a fabric according to the method provided above.

Dry fabric odor (DFO) is assessed using headspace analysis, and the results are provided in Table 3B.

TABLE 3B

| Premix # | Plant Rosin Material Trade Name | Wt % | Benefit Agent Type | Wt % | DFO Headspace (nM/L) |
|---|---|---|---|---|---|
| 1 | Permalyn 5095 | 0% | Perfume | 100% | 0.08 |
| 2 | Permalyn 5095 | 60% | Perfume | 40% | 52 |
| 3 | Permalyn 5095 | 70% | Perfume | 30% | 62 |
| 4 | Permalyn 5095 | 80% | Perfume | 20% | 110 |

As shown in Table 3B, perfume in the DFO Headspace (nM/L) increases as the amount of plant rosin material in the premix increases.

Additionally, micrographs of the final liquid conditioning products made with Premixes 1, 2, 3, and 4 are obtained. As shown in FIG. 6, particles are visibly present in the liquid compositions made with Premixes 2, 3, and 4. Furthermore, it appears that the particles are relatively larger in the compositions that include premixes having relatively larger amounts of the plant rosin material; see, e.g., the micrographs of the products made with Premixes 3 and 4.

Figure 6A:
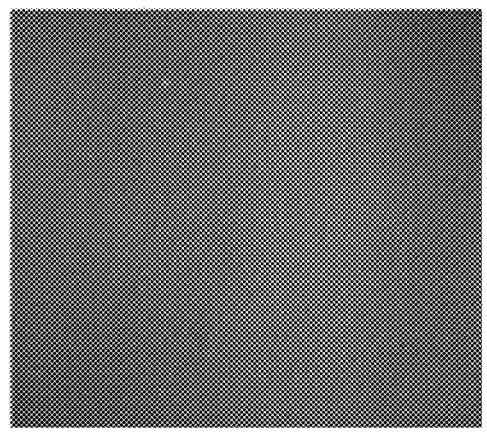
FIG. 6A shows a liquid treatment composition made with Premix #1, as described in Example 3 below.
Figure 6B:
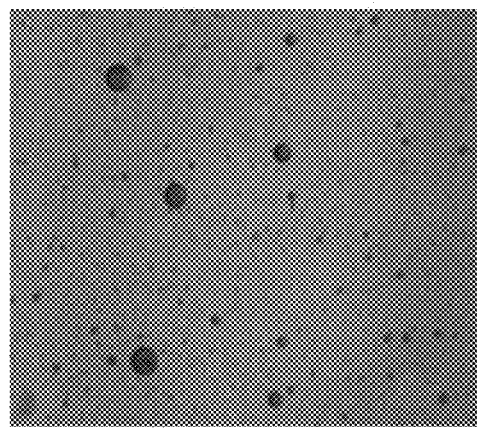
FIG. 6B shows a liquid treatment composition made with Premix #2, as described in Example 3 below.
Figure 6C:
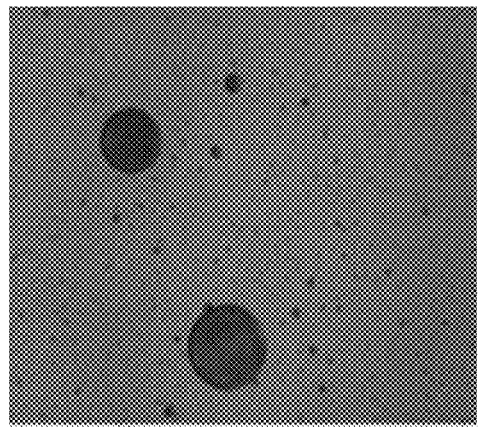
FIG. 6C shows a liquid treatment composition made with Premix #3, as described in Example 3 below.
Figure 6D:
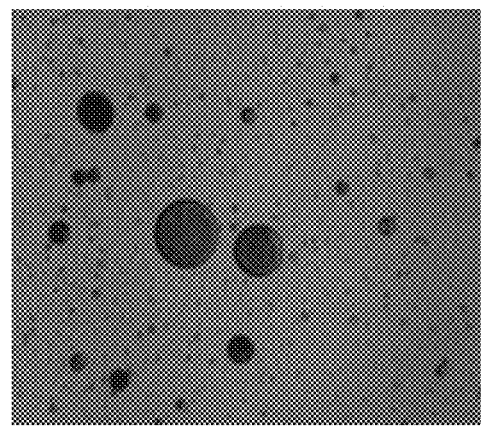
FIG. 6D shows a liquid treatment composition made with Premix #4, as described in Example 3 below.

Additionally, micrographs of the final liquid conditioning products made with Premixes 1, 2, 3, and 4 are obtained, at 10× magnification with polarized transmitted light. As shown in FIG. 6A, particles are not visible in a liquid composition made with Premix 1, which does not include a plant rosin material. As shown in FIGS. 6B-6D, particles are visibly present in the liquid compositions made with Premixes 2 (FIG. 6B), 3 (FIG. 6C), and 4 (FIG. 6D). Furthermore, it appears that the particles are relatively larger in the compositions that include premixes having relatively larger amounts of the plant rosin material; see, e.g., the micrographs of the products made with Premixes 3 (FIG. 6C) and 4 (FIG. 6D).

Example 4. Freshness Benefits

A liquid fabric (LFE) base composition according to Table 4A, below, is provided.

TABLE 4A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Structuring agent[2] | 0.2% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])
[2]FLOSOFT ™ FS 222 (ex SNF Floerger ®)

The following rosin/perfume premixes are prepared, some with an emulsifying agent, as shown in Table 4B. The weight percentages are based on weight of the premix composition.

TABLE 4B

| Premix # | Plant Rosin Material Type | Wt % | Benefit Agent Type | Wt % | Emulsifying agent Type | Wt % |
|---|---|---|---|---|---|---|
| 1 | Permalyn 5095 | 70% | Perfume | 30% | — | — |
| 2 | Permalyn 5095 | 25% | Perfume | 40% | Soluplus | 35% |
| 3 | Permalyn 5110 | 70% | Perfume | 30% | — | — |
| 4 | Permalyn 5110 | 25% | Perfume | 40% | Soluplus | 35% |
| 5 | Poly-Pale | 25% | Perfume | 40% | Soluplus | 35% |
| 6 | Foral 85 | 70% | Perfume | 30% | — | — |
| 7 | Foral 85 | 25% | Perfume | 40% | Soluplus | 35% |
| 8 | Abalyn D-E | 70% | Perfume | 30% | — | — |
| 9 | Deresinate TX | 70% | Perfume | 30% | — | — |
| 10 | Foralyn E | 70% | Perfume | 30% | — | — |
| 11 | Gum Rosin | 25% | Perfume | 40% | Soluplus | 35% |
| 12 | Gum Rosin | 70% | Perfume | 30% | — | — |
| 13 | Lurefor 125 | 25% | Perfume | 40% | Soluplus | 35% |
| 14 | Foral 105 | 25% | Perfume | 40% | Soluplus | 35% |
| 15 | Staybelite Resin E | 70% | Perfume | 30% | — | — |
| 16 | Zincogral Z | 25% | Perfume | 40% | Soluplus | 35% |

Various liquid fabric conditioning products are made with the premixes in Table 4B and added to the composition of Table 4A. For each leg, a parallel product is made that only adds the perfume (no premix; no plant rosin material) which is used as reference product. Premixes in Table 4B are added in an amount to deliver the same amount of perfume to respect of the reference product (no premix, no plant rosin material). The premixes can be added to the composition of Table 4A while overhead mixing or while mixing with Ultraturrax®.

TABLE 4C

| Leg | Premix used in LFE | Plant Rosin Material | Perfume level (wt %) | Procedure of addition of premix |
|---|---|---|---|---|
| A | 1 | Permalyn 5095 | 1.0% | Overhead mixing |
| B | 2 | Permalyn 5095 | 1.0% | Overhead mixing |
| C | 3 | Permalyn 5110 | 1.0% | Overhead mixing |
| D | 4 | Permalyn 5110 | 1.0% | Overhead mixing |
| E | 5 | Poly-Pale | 1.0% | Overhead mixing |
| F | 6 | Foral 85 | 1.0% | Overhead mixing |
| G | 7 | Foral 85 | 1.0% | Overhead mixing |
| H | 8 | Abalyn D-E | 0.6% | UltraTurrax ® |
| I | 9 | Deresinate TX | 0.6% | UltraTurrax ® |
| J | 10 | Foralyn E | 0.6% | UltraTurrax ® |
| K | 11 | Gum Rosin | 0.3% | Overhead mixing |
| L | 12 | Gum Rosin | 0.3% | Overhead mixing |
| M | 13 | Lurefor 125 | 0.3% | Overhead mixing |
| N | 14 | Foral 105 | 1.0% | Overhead mixing |
| O | 15 | Staybelite Resin E | 0.6% | UltraTurrax ® |

The products are used to treat fabrics according to the method provided above, and the dry fabric odor (DFO) for each is measured. The formulation of the LFE composition is reported in Table 4B:

The results are provided in Table 4D below. Additionally, Table 4D shows the "Delta DFO," showing the difference between the DFO scores for the products that include the premixes of Table 4B and the products that only include the perfume. Furthermore, the "DFO Ratio" is the ratio of the two DFO scores in that leg. Relatively higher Delta DFO scores and DFO Ratios indicate that the formulations comprising the premixes are providing freshness benefit compared to perfume-only formulations.

Additionally, a comment on dispersibility is provided for the premixes, based on observations made while trying to disperse the premix into the LFE base composition. Premix 16 was not tested.

TABLE 4D

| Leg | Premix used in LFE | Plant Rosin Material | DFO Headspace (nM/L) (perfume + plant rosin) | DFO Headspace (nM/L) (perfume only) | Delta DFO | DFO Ratio | Dispersibility of Premix (1-5) [2] |
|---|---|---|---|---|---|---|---|
| A | 1 | Permalyn 5095 | 60.2 | 6.12 | +54.08 | 9.8 | 3 |
| B | 2 | Permalyn 5095 | 17.8 | 6.12 | +11.68 | 2.9 | 3 |
| C | 3 | Permalyn 5110 | 149.0 | 4.61 | +144.39 | 32.3 | 4 |
| D | 4 | Permalyn 5110 | 15.9 | 6.12 | +9.78 | 2.6 | 3 |
| E | 5 | Poly-Pale | 8.68 | 6.12 | +2.56 | 1.4 | 2 |

TABLE 4D-continued

| Leg | Premix used in LFE | Plant Rosin Material | DFO Headspace (nM/L) (perfume + plant rosin) | DFO Headspace (nM/L) (perfume only) | Delta DFO | DFO Ratio | Dispersibility of Premix (1-5) [2] |
|---|---|---|---|---|---|---|---|
| F | 6 | Foral 85 | 88.54 | 4.61 | +83.93 | 19.2 | 3 |
| G | 7 | Foral 85 | 8 | 6.12 | +1.88 | 1.3 | 2 |
| H | 8 | Abalyn D-E | 2.57 | 0.33 | +2.24 | 7.8 | 1 |
| I | 9 | Deresinate | 2.12 | 0.33 | +1.79 | 6.4 | 1 |
| J | 10 | Foralyn E | 44.23 | 0.33 | +43.9 | 134.0 | 4 |
| K | 11 | Gum Rosin | 0.69 | 0.59 | +0.1 | 1.2 | 3 |
| L | 12 | Gum Rosin | 1.58 | 0.59 | +0.99 | 2.7 | 5 |
| M | 13 | Lurefor 125 | 1.57 | 0.59 | +0.98 | 2.7 | 3 |
| N | 14 | Foral 105 | 16.6 | 6.12 | +10.48 | 2.7 | 2 |
| O | 15 | Staybelite Resin E | 2.12 | 0.33 | +1.79 | 6.4 | 1 |

[2] Dispersibility is relative to the ease of dispersing the rosin/perfume (and emulsifying agent, if any) premix in the finished product formulation, where 5 = very difficult to disperse, 3 = average dispersibility, and 1 = good dispersibility.

Figure 7A:
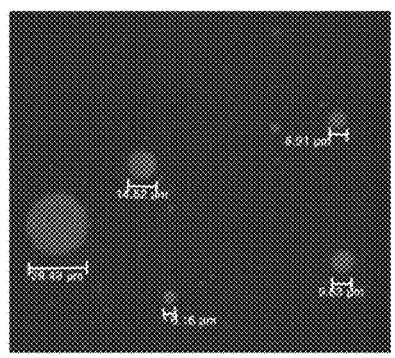
FIG. 7A shows a liquid fabric conditioning product made according to Leg A, as described in Example 4 below.
Figure 7B:
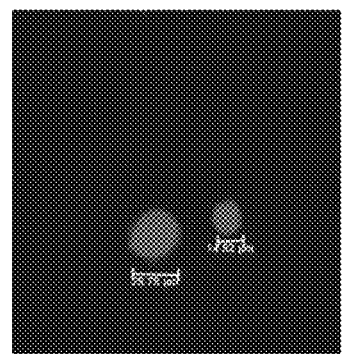
FIG. 7B shows a liquid fabric conditioning product made according to Leg D, as described in Example 4 below.
Figure 7C:
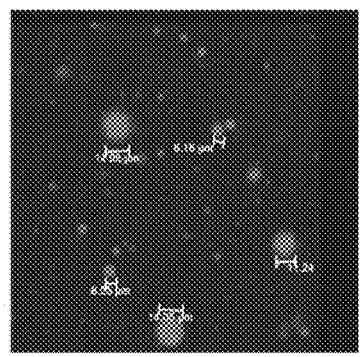
FIG. 7C shows a liquid fabric conditioning product made according to Leg G, as described in Example 4 below.

Additionally, micrographs of some of the liquid fabric conditioning products are provided in FIGS. 7A, 7B, and 7C. The micrographs taken with fluorescence confocal laser scanning microscopy (CLSM), at a magnification of 63×. The figures show micrographs of samples of the premix-containing products from Leg A (FIG. 7A), Leg D (FIG. 7B), and Leg G (FIG. 7C) at 63×. Particles can be seen in each of the products.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making a treatment composition, the process comprising the steps of:
   providing a base composition,
      wherein the base composition comprises an adjunct material; and
   adding a plant rosin material and one or more benefit agents to the base composition, wherein the plant rosin material is added with or after the one or more benefit agents and the plant rosin material comprises a plant rosin ester comprising glycerol, pentaerythritol, or both.

2. The process according to claim 1, wherein the plant rosin material is added with the one or more benefit agents.

3. The process according to claim 2, wherein the plant rosin material and the one or more benefit agents are added in a single input stream as a premix composition to the base composition.

4. The process according to claim 3, wherein the premix composition comprises:
   from about 5% to about 95% of the plant rosin material, and
   from about 5% to about 95% of the one or more benefit agents.

5. The process according to claim 1, wherein the process further comprises heating the plant rosin material above ambient temperature prior to combining the plant rosin material with the one or more benefit agent, with the base composition, or both.

6. The process according to claim 1, wherein the process further comprising the step of combining the plant rosin material and the one or more benefit agents at ambient temperature,
   wherein the weight ratio of plant rosin material to benefit agent is less than 50:50, and
   wherein the one or more benefit agents comprises perfume raw materials.

7. The process according to claim 1, wherein the plant rosin material is provided as a powder characterized by particles having an average diameter of less than 5 mm,
   optionally wherein the process further comprises the step of grinding or pulverizing larger pieces of the plant rosin materials to form the powder.

8. The process according to claim 1, wherein the plant rosin material comprises a material selected from the group consisting of gum rosin, wood rosin, tall oil rosin, derivatives thereof, and mixtures thereof.

9. The process according to claim 1, wherein the one or more benefit agents comprises a fragrance material.

10. The process according to claim 1, wherein the base composition is a liquid.

11. The process according to claim 1, wherein the base composition comprises at least 8% water, by weight of the base composition.

12. The process according to claim 1, wherein the adjunct ingredient comprises a surfactant system, fabric softening agents, or combinations thereof.

13. The process according to claim 1, wherein the plant rosin material and the one or more benefit agents are combined with the base composition via a batch process, via a continuous-loop addition process, or via an in-line addition process.

14. The process according to claim 1, wherein the plant rosin material and the one or more benefit agents are combined with the base composition via an in-line process and mixed with a dynamic mixer, characterized by a tangential velocity of from about 7 m/s to about 19 m/s.

15. The process according to claim 1, wherein the treatment composition made from the process comprises particles, wherein the particles comprise the plant resin material and the one or more benefit agents.

16. The process according to claim 1, wherein the treatment composition is a liquid, and wherein the process further comprises adding a structuring agent.

17. The process according to claim 1, wherein the treatment composition is a consumer product composition,
   wherein the consumer product composition is a fabric care composition, a hard surface cleaner composition, a dish care composition, a hair care composition, a body cleansing composition, or a mixture thereof.

18. The process according to claim 1, wherein the treatment composition is a liquid.

19. The process according to claim 4, wherein the premix composition comprises less than 5%, by weight of the premix composition, of water.

* * * * *